US009615955B2

(12) United States Patent
Bledsoe

(10) Patent No.: US 9,615,955 B2
(45) Date of Patent: Apr. 11, 2017

(54) ORTHOPEDIC KNEE BRACE WITH DYNAMICALLY CHANGING MEDIAL AND LATERAL HINGES

(75) Inventor: Brett Owen Bledsoe, Cedar Hill, TX (US)

(73) Assignee: Breg, Inc., Carlsbad, CA (US)

(*) Notice: Subject to any disclaimer, the term of this patent is extended or adjusted under 35 U.S.C. 154(b) by 140 days.

(21) Appl. No.: 13/091,885

(22) Filed: Apr. 21, 2011

(65) Prior Publication Data

US 2012/0271211 A1    Oct. 25, 2012

(51) Int. Cl.
*A61F 5/00* (2006.01)
*A61F 5/01* (2006.01)

(52) U.S. Cl.
CPC .... *A61F 5/0123* (2013.01); *A61F 2005/0139* (2013.01); *A61F 2005/0144* (2013.01); *A61F 2005/0146* (2013.01); *A61F 2005/0153* (2013.01)

(58) Field of Classification Search
CPC ............ A61F 5/0123; A61F 2005/0139; A61F 2005/0153; A61F 2005/0146; A61F 2005/0144; A61F 2005/0132; A61F 5/0125; A61F 5/013; A61F 5/0102; A61F 5/01; A61F 2005/0134; A61F 2005/0137; A61F 2005/0141; A61F 2005/0148; A61F 2005/0151; A61F 2005/0155; A61F 2005/0165; A61F 2005/0167; A61F 2005/0169; A61F 2005/0179; A61F 2005/0158; A61F 2005/016; A61F 2005/0162
USPC ................................ 602/16, 26, 23; 128/882
See application file for complete search history.

(56) References Cited

U.S. PATENT DOCUMENTS

| 21,872 A | 10/1858 | Bunce |
|---|---|---|
| 552,143 A | 12/1895 | Rankin |
| 1,381,290 A | 6/1921 | Diadul |
| 2,250,493 A | 7/1941 | Milne |

(Continued)

FOREIGN PATENT DOCUMENTS

| DE | 170739 | 5/1906 |
|---|---|---|
| DE | 357243 | 8/1922 |

(Continued)

OTHER PUBLICATIONS

Komistek, Richard D. et al., "An In Vitro Analysis of the Effectiveness of the Osteoarthritic Knee Brace During Heel Strike of Gait," 1999, 12 pages, vol. 14, No. 6, Journal of Arthroplasty (printed from Bledsoe Brace Systems website: http://bledsoebrace.com/studies/rose.htm).

(Continued)

*Primary Examiner* — Victoria J Hicks
(74) *Attorney, Agent, or Firm* — Rodney F. Brown

(57) ABSTRACT

An orthopedic knee brace includes an upper medial upright; a lower medial upright; an upper lateral upright; a lower lateral upright; a medial hinge connected rotatably to the upper and lower medial uprights; a lateral hinge connected rotatably to the upper and lower lateral uprights; and wherein one of the medial and lateral hinges is configured such that its respective uprights rotate from a flexion to an extended relative positioning while striking a radially-decreasing arc, while the other of the medial and lateral hinges is configured such that its respective uprights rotate from a flexion to an extended relative positioning while striking a radially-increasing arc.

15 Claims, 20 Drawing Sheets

(56) References Cited

U.S. PATENT DOCUMENTS

| | | |
|---|---|---|
| 2,558,986 A | 7/1951 | Seelert |
| 3,046,981 A | 7/1962 | Biggs et al. |
| 3,785,371 A | 1/1974 | Lewis |
| 3,805,773 A | 4/1974 | Sichau |
| 3,817,244 A | 6/1974 | Taylor |
| 3,902,482 A | 9/1975 | Taylor |
| 4,057,056 A | 11/1977 | Payton |
| 4,057,853 A | 11/1977 | McLane |
| 4,090,508 A | 5/1978 | Gaylord, Jr. |
| 4,115,902 A | 9/1978 | Taylor |
| 4,220,148 A | 9/1980 | Lehneis |
| 4,240,414 A | 12/1980 | Theisler |
| 4,256,097 A | 3/1981 | Willis |
| 4,271,831 A | 6/1981 | Deibert |
| 4,337,764 A | 7/1982 | Lerman |
| 4,340,041 A | 7/1982 | Frank |
| 4,361,142 A | 11/1982 | Lewis et al. |
| 4,370,977 A | 2/1983 | Mauldin et al. |
| 4,379,463 A | 4/1983 | Meier et al. |
| 4,381,768 A | 5/1983 | Erichsen et al. |
| D269,379 S | 6/1983 | Bledsoe |
| 4,463,751 A | 8/1984 | Bledsoe |
| 4,487,200 A | 12/1984 | Feanny et al. |
| 4,506,661 A | 3/1985 | Foster |
| 4,531,731 A | 7/1985 | Law |
| 4,554,913 A | 11/1985 | Womack et al. |
| 4,556,053 A | 12/1985 | Irons |
| 4,565,190 A | 1/1986 | Pirmantgen et al. |
| 4,572,170 A | 2/1986 | Cronk et al. |
| 4,573,455 A | 3/1986 | Hoy |
| 4,599,998 A | 7/1986 | Castillo |
| 4,614,181 A | 9/1986 | Karlsson |
| 4,620,532 A | 11/1986 | Houswerth |
| 4,624,247 A | 11/1986 | Ford |
| 4,632,097 A | 12/1986 | Brooks |
| 4,632,098 A | 12/1986 | Grundei et al. |
| 4,633,867 A | 1/1987 | Kausek et al. |
| 4,635,623 A | 1/1987 | Charuest et al. |
| 4,649,906 A | 3/1987 | Spademan |
| 4,697,583 A | 10/1987 | Mason et al. |
| 4,699,129 A | 10/1987 | Aaserude et al. |
| 4,723,539 A | 2/1988 | Townsend |
| 4,765,318 A | 8/1988 | Tranberg et al. |
| 4,781,180 A | 11/1988 | Solomonow |
| 4,791,916 A | 12/1988 | Paez |
| 4,793,333 A | 12/1988 | Marquette |
| 4,796,610 A | 1/1989 | Cromartie |
| 4,803,975 A | 2/1989 | Meyers |
| 4,805,606 A | 2/1989 | McDavid, III |
| 4,817,588 A | 4/1989 | Bledsoe |
| 4,846,842 A | 7/1989 | Connolly et al. |
| 4,856,501 A | 8/1989 | Castillo et al. |
| 4,881,532 A | 11/1989 | Borig et al. |
| 4,940,045 A | 7/1990 | Cromartie |
| 4,955,369 A | 9/1990 | Bledsoe et al. |
| 5,056,509 A | 10/1991 | Swearington |
| 5,107,824 A | 4/1992 | Rogers et al. |
| 5,131,385 A | 7/1992 | Kuehnegger et al. |
| 5,259,832 A | 11/1993 | Townsend et al. |
| 5,277,698 A | 1/1994 | Taylor |
| 5,295,303 A | 3/1994 | Ogawa et al. |
| 5,302,169 A | 4/1994 | Taylor |
| 5,316,547 A | 5/1994 | Gildersleeve |
| 5,383,845 A | 1/1995 | Nebolon |
| 5,400,806 A | 3/1995 | Taylor |
| 5,409,449 A | 4/1995 | Nebolon |
| 5,415,625 A | 5/1995 | Cassford et al. |
| 5,454,383 A | 10/1995 | Nebolon |
| 5,456,659 A | 10/1995 | Gildersleeve et al. |
| 5,458,565 A | 10/1995 | Tillinghast, III et al. |
| 5,520,622 A | 5/1996 | Bastyr et al. |
| 5,527,268 A | 6/1996 | Gildersleeve et al. |
| D372,983 S | 8/1996 | Nebolon |
| 5,542,911 A | 8/1996 | Cassford et al. |
| 5,586,970 A | 12/1996 | Morris et al. |
| 5,611,774 A | 3/1997 | Postelmans |
| 5,662,596 A | 9/1997 | Young |
| 5,672,152 A | 9/1997 | Mason et al. |
| 5,743,865 A | 4/1998 | Townsend |
| 5,766,140 A | 6/1998 | Tillinghast, III et al. |
| 5,772,618 A | 6/1998 | Mason et al. |
| 5,782,780 A | 7/1998 | Mason et al. |
| 5,788,618 A | 8/1998 | Joutras |
| 5,807,294 A | 9/1998 | Cawley et al. |
| 5,827,208 A | 10/1998 | Mason et al. |
| 5,954,621 A | 9/1999 | Joutras et al. |
| 5,976,063 A | 11/1999 | Joutras et al. |
| 6,413,232 B1 | 7/2002 | Townsend et al. |
| 6,527,733 B1 | 3/2003 | Ceriani et al. |
| 6,752,775 B2 | 6/2004 | Seligman et al. |
| 6,936,019 B2 | 8/2005 | Mason |
| 6,960,177 B2 | 11/2005 | Turrini et al. |
| 6,969,364 B2 | 11/2005 | Sterling |
| 7,059,329 B2 | 6/2006 | Mason et al. |
| 7,060,045 B2 | 6/2006 | Mason et al. |
| 7,201,728 B2 | 4/2007 | Sterling |
| 7,235,059 B2 | 6/2007 | Mason et al. |
| 7,311,687 B2 | 12/2007 | Hoffmeier et al. |
| 7,479,122 B2 | 1/2009 | Ceriani et al. |
| 7,485,103 B2 | 2/2009 | Mason et al. |
| 7,500,957 B2 | 3/2009 | Bledsoe |
| 2004/0002674 A1 | 1/2004 | Sterling |
| 2006/0206045 A1 | 9/2006 | Townsend et al. |
| 2008/0208095 A1 | 8/2008 | Kazmierczak et al. |
| 2008/0319363 A1 | 12/2008 | Pansiera |
| 2010/0010409 A1 | 1/2010 | Bejarano |

FOREIGN PATENT DOCUMENTS

| | | |
|---|---|---|
| DE | 846895 | 8/1952 |
| DE | 1024204 | 2/1958 |
| DE | 2239382 | 2/1974 |
| DE | 19945829 | 4/2001 |
| GB | 110209 | 10/1917 |
| GB | 1449554 | 9/1976 |
| GB | 2136294 | 9/1984 |
| GB | 2163352 | 2/1986 |
| JP | 2006-175143 | 7/2006 |
| WO | 8502536 | 6/1985 |
| WO | 9729717 | 8/1997 |
| WO | WO2005099638 | 10/2005 |

OTHER PUBLICATIONS

Hewitt, Timothy E. et al., "Decrease in Knee Joint Pain and Increase in Function in Patients with Medical Compartment Arthroris: A Perspective Analysis of Valgus Bracing," 1998, 16 pages, vol. 21, No. 2, Orthopedics (printed from Bledsoe Brace Systems website: http://bledsoebrace.com/studies/cinci.htm).

International Preliminary Report on Patentability for International Patent Application No. PCT/US2011/033538 mailed on Aug. 13, 2013.

Japanese Office Action Dec. 22, 2015 in corresponding Japanese Application No. 2014-506375.

Extended European search report for European patent application No. 15001509.7 dated Oct. 2, 2015 (7 pages).

Japanese Office Action mailed Mar. 19, 2015 in corresponding Japanese Application No. 2014-506375.

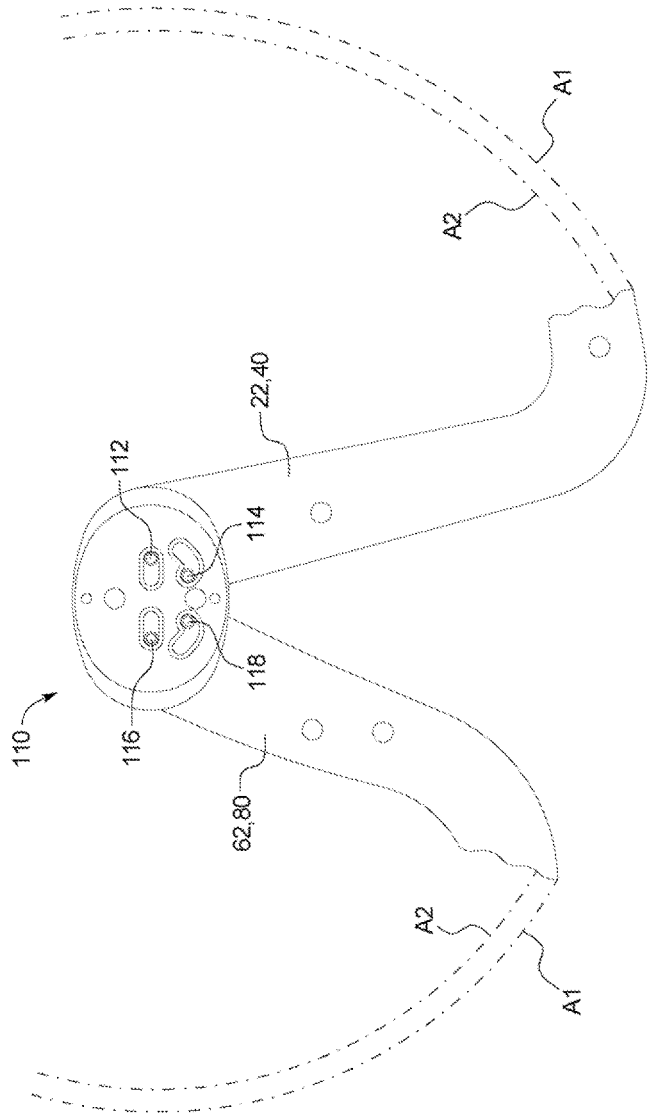

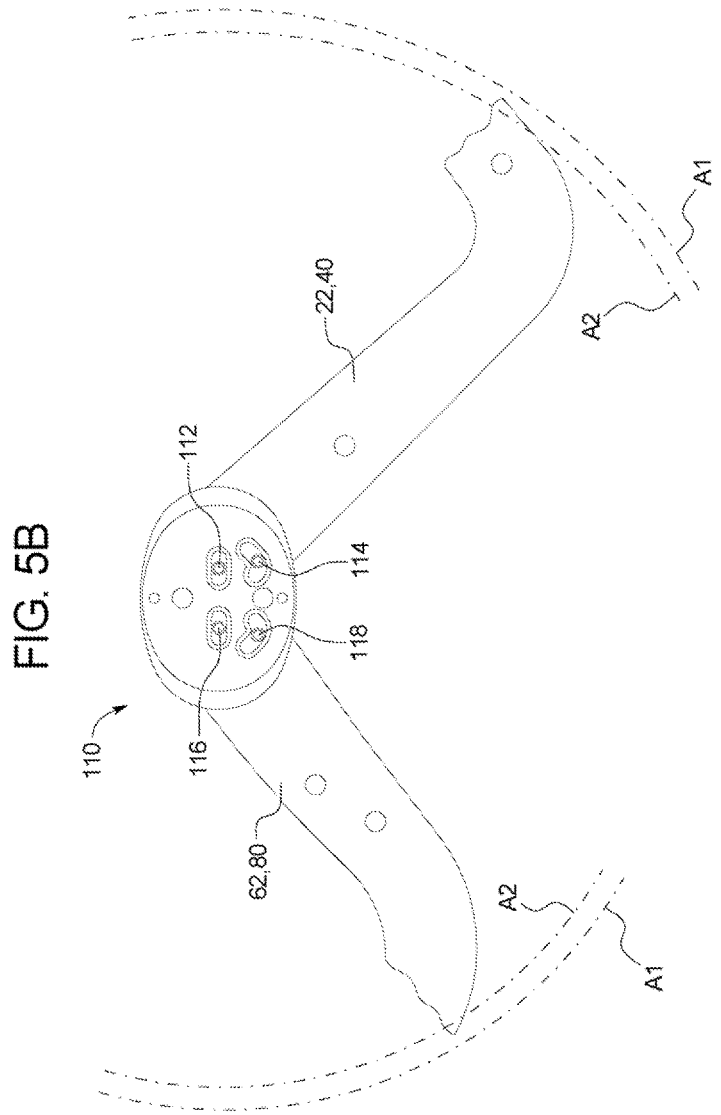

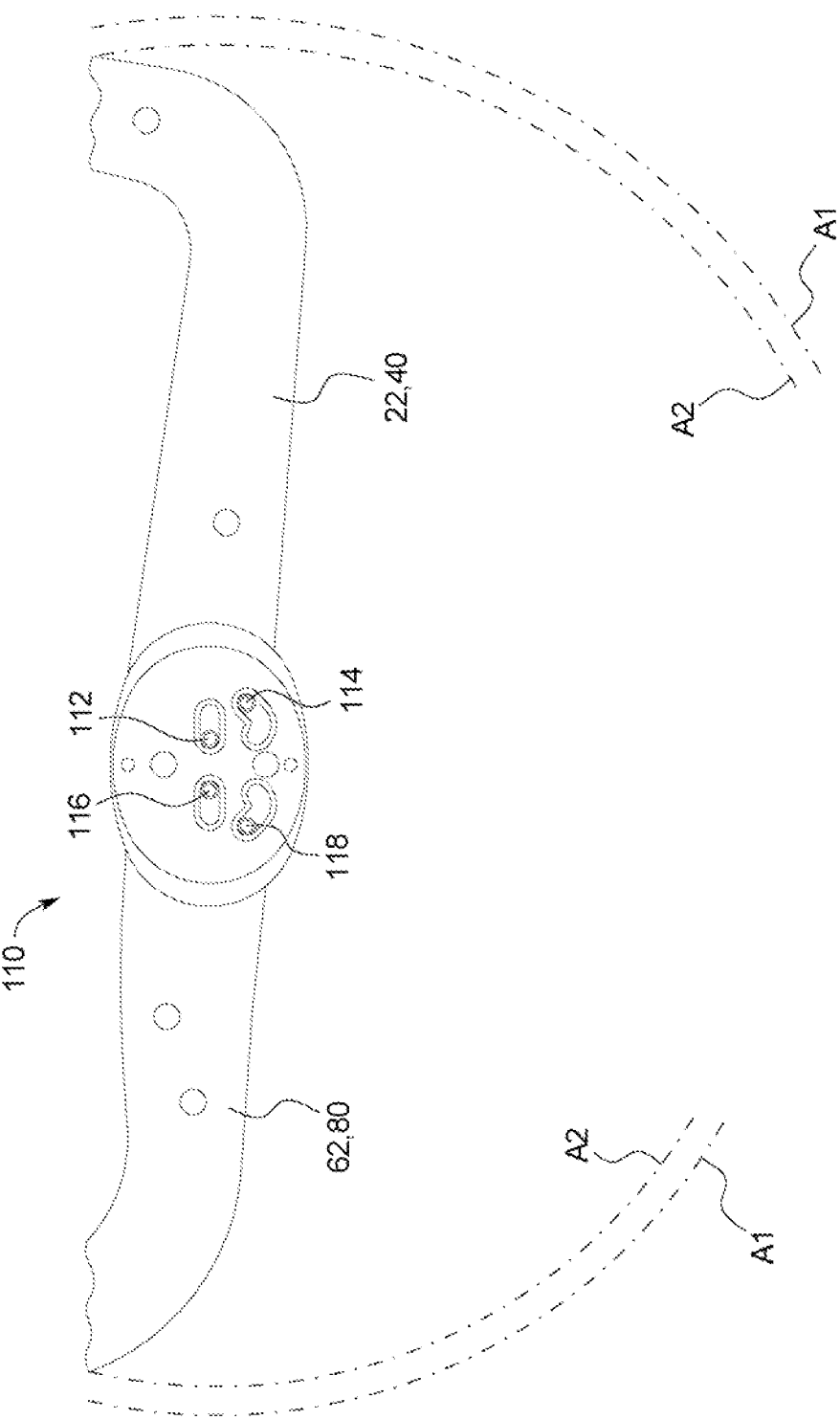

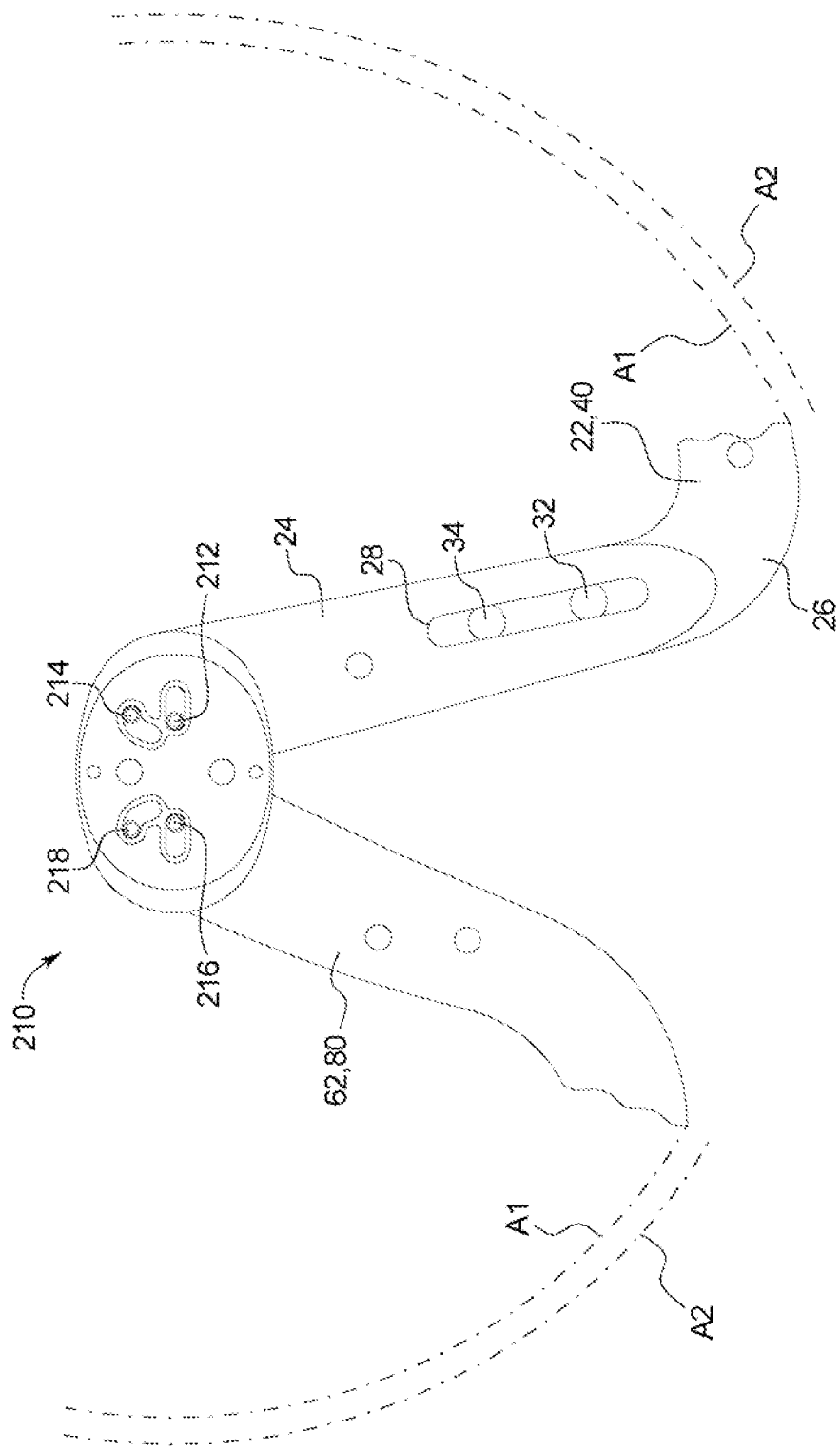

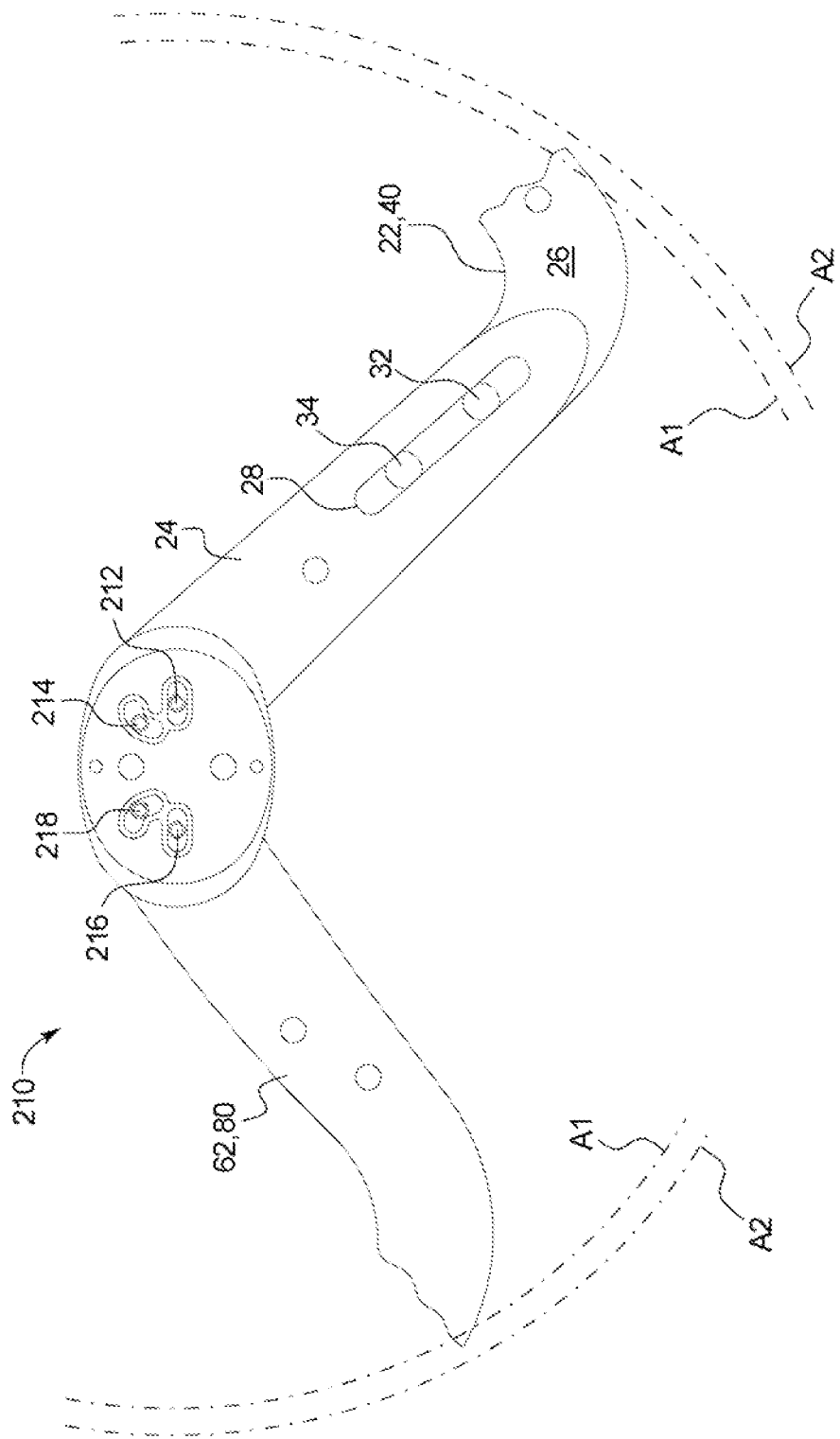

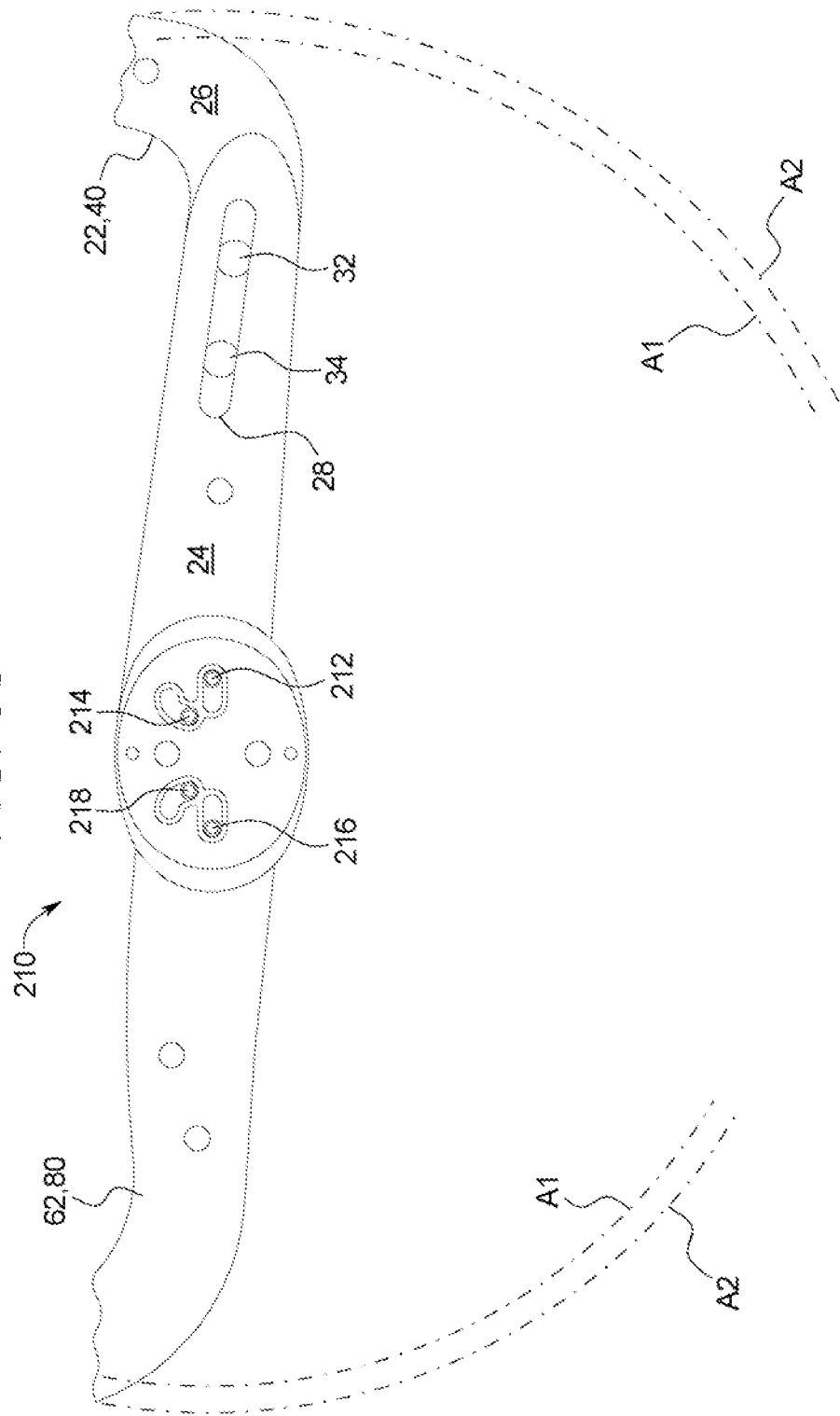

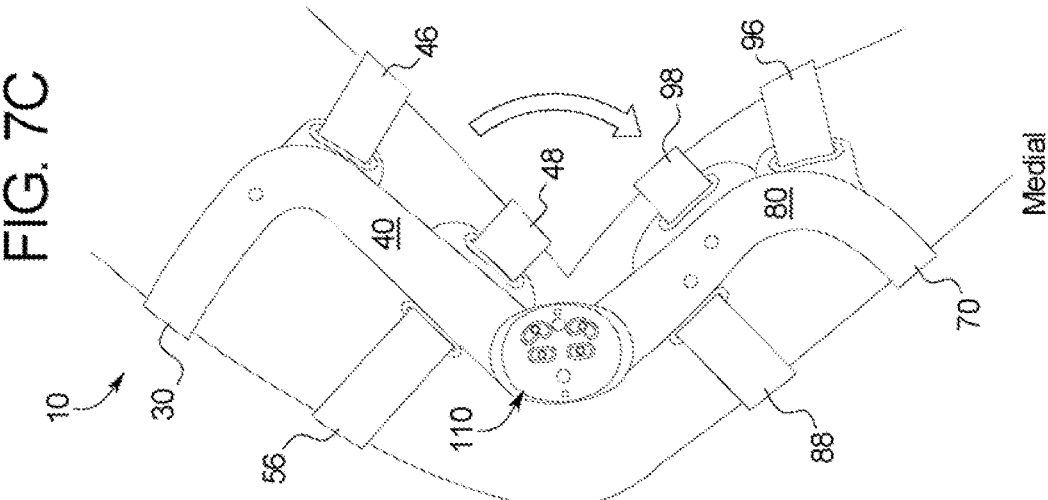
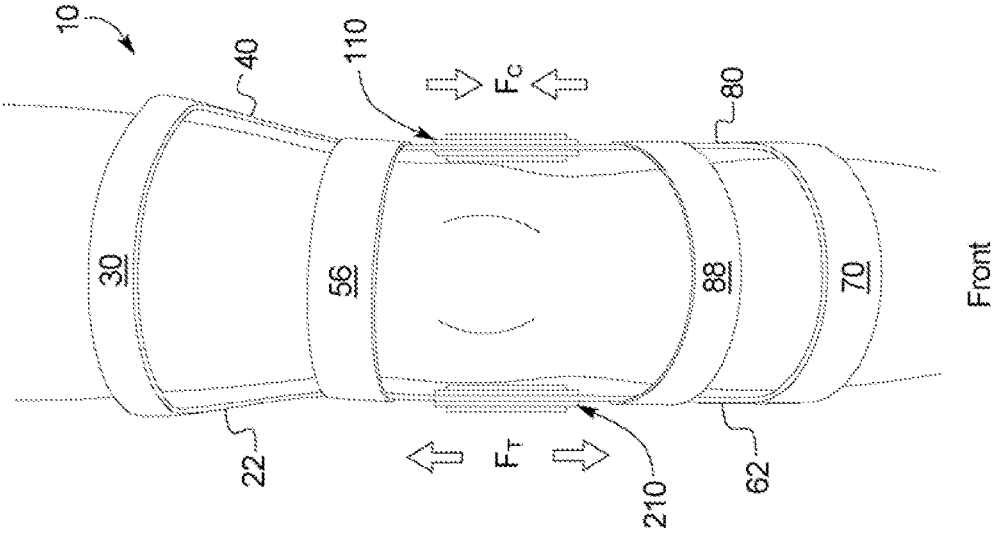
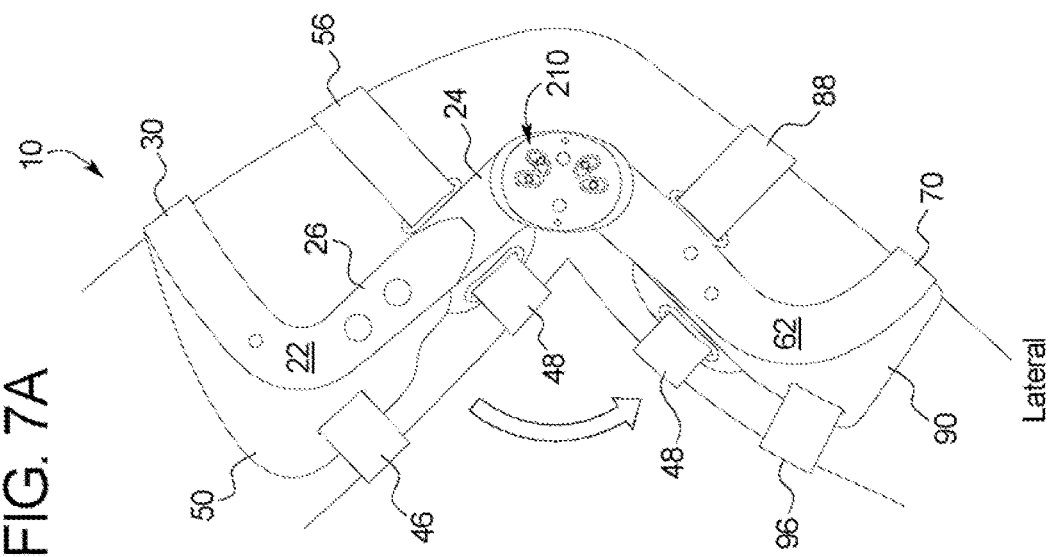

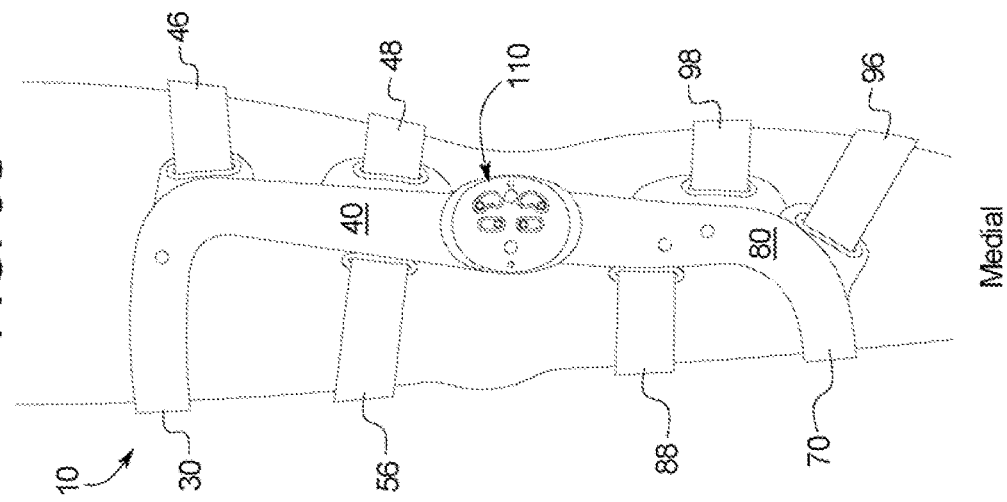
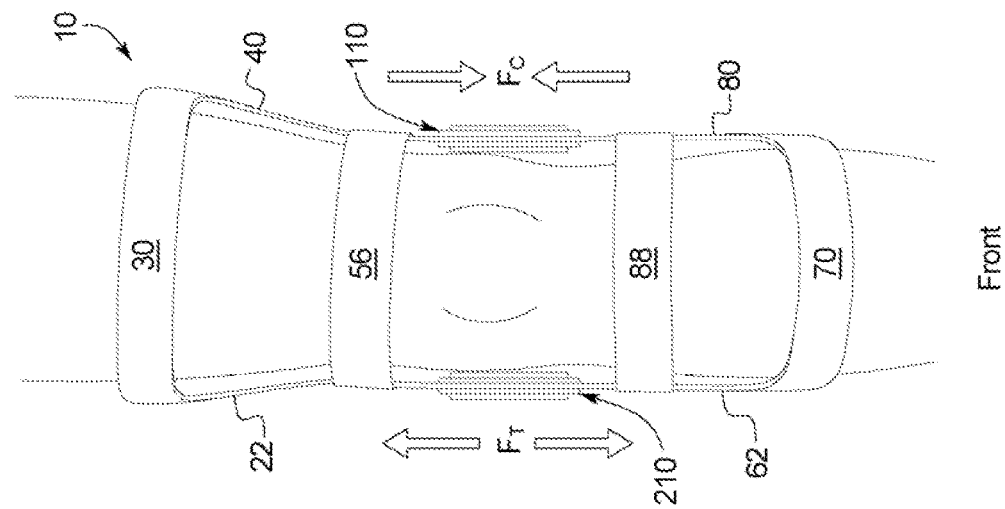
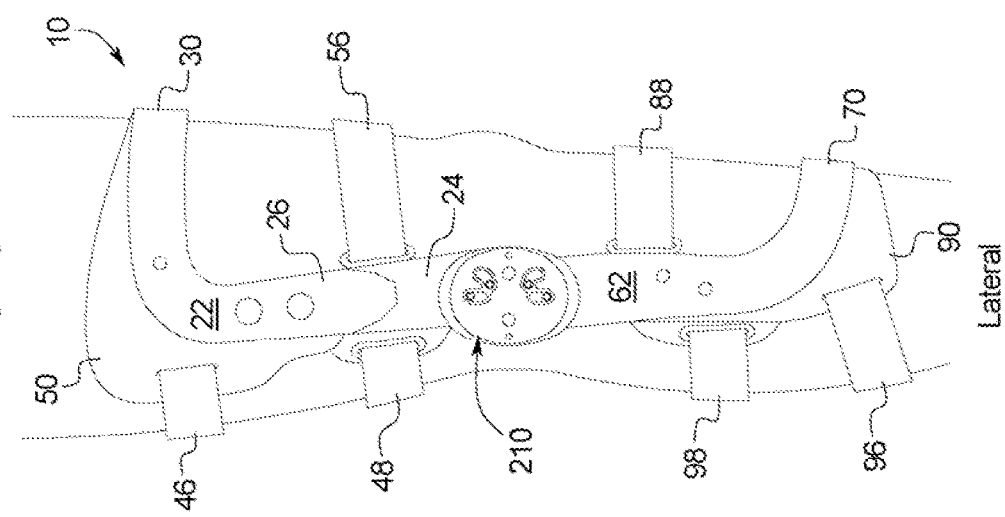

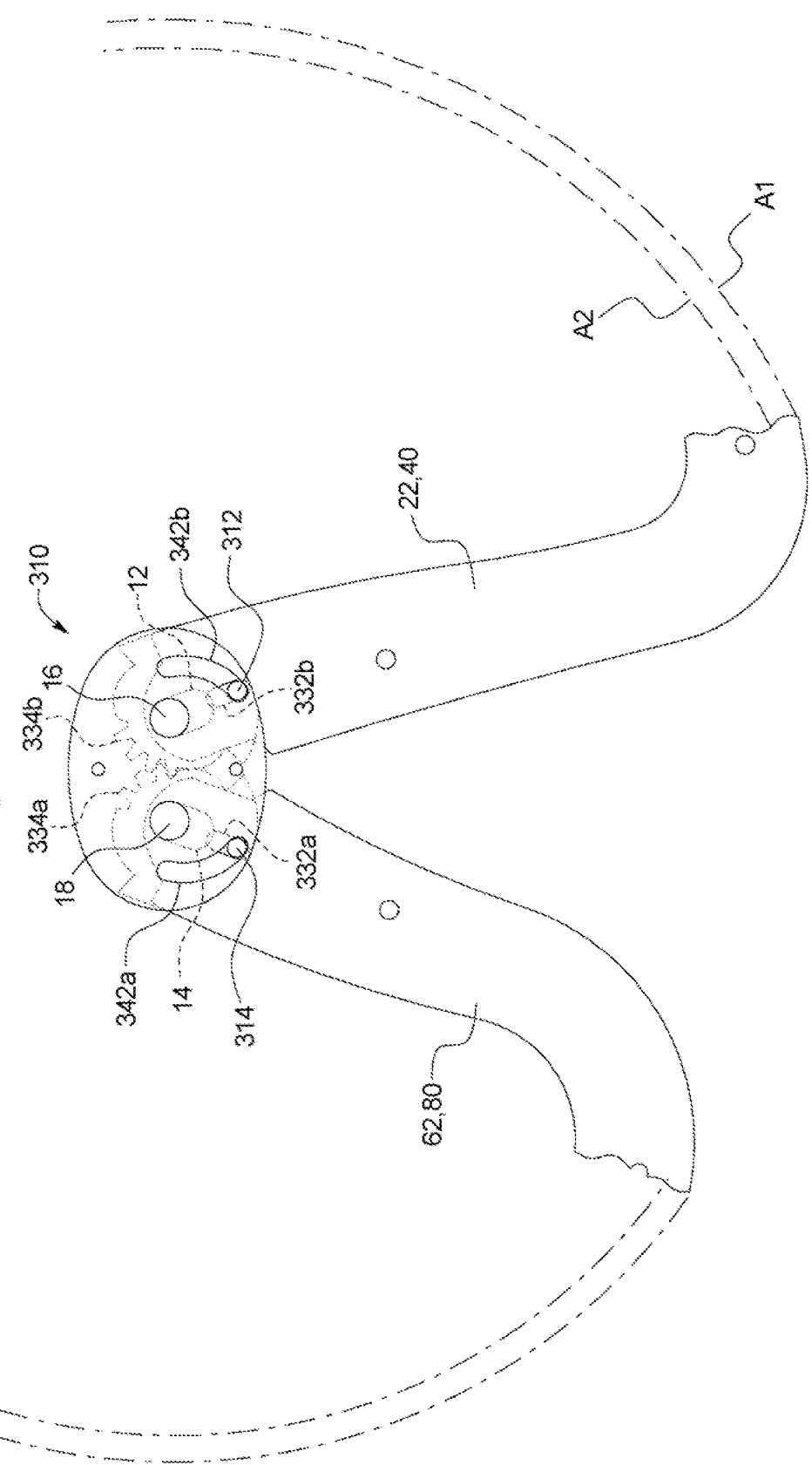

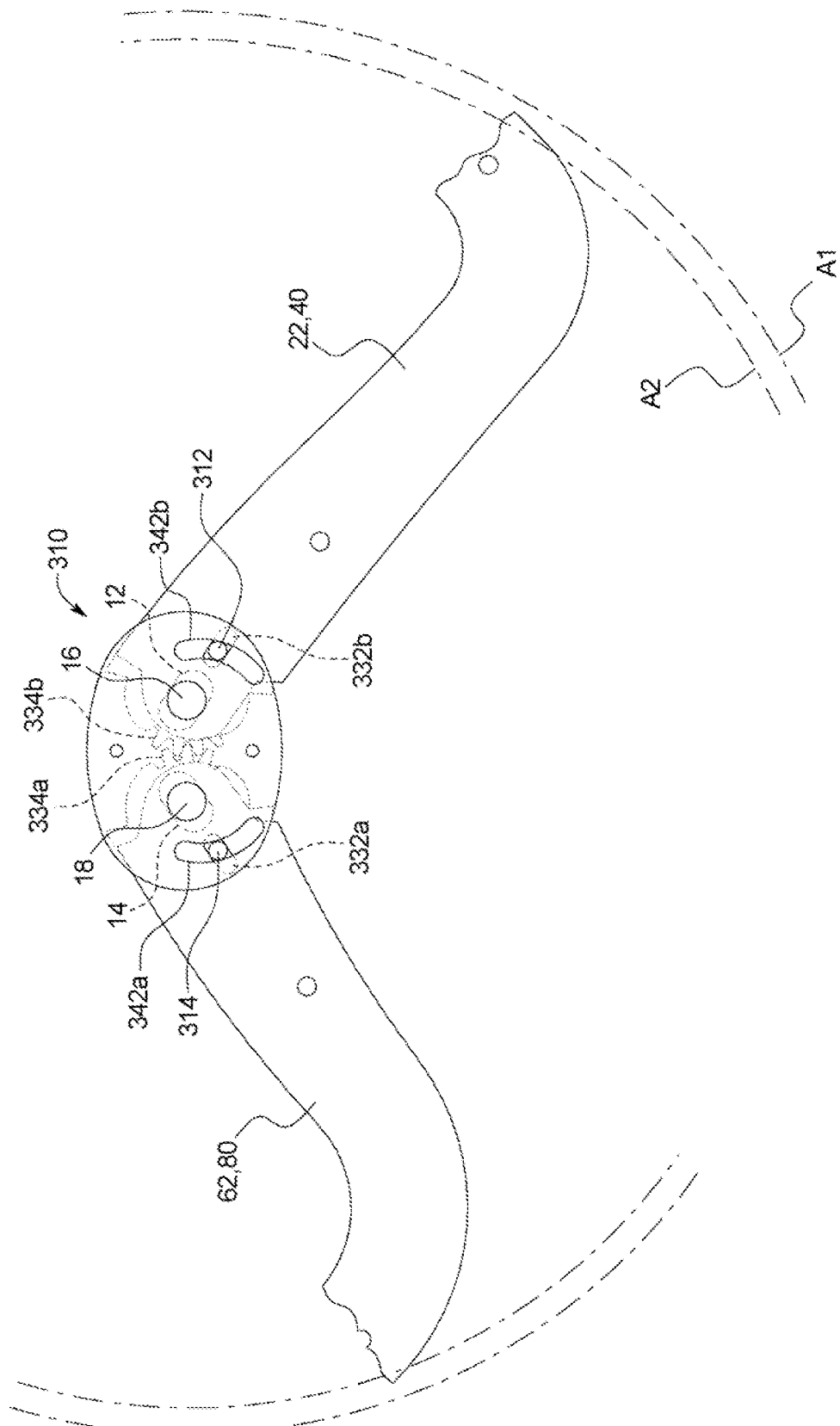

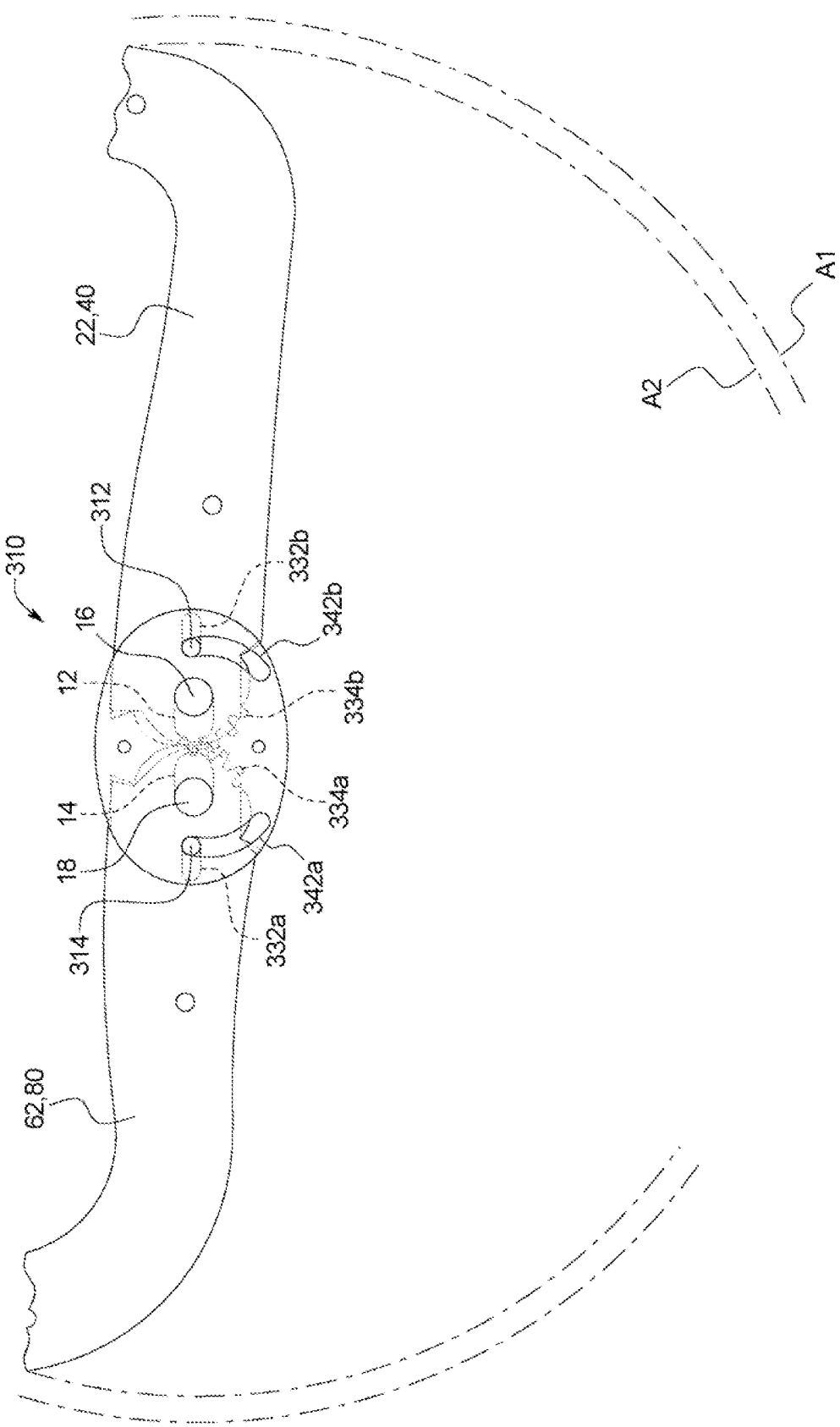

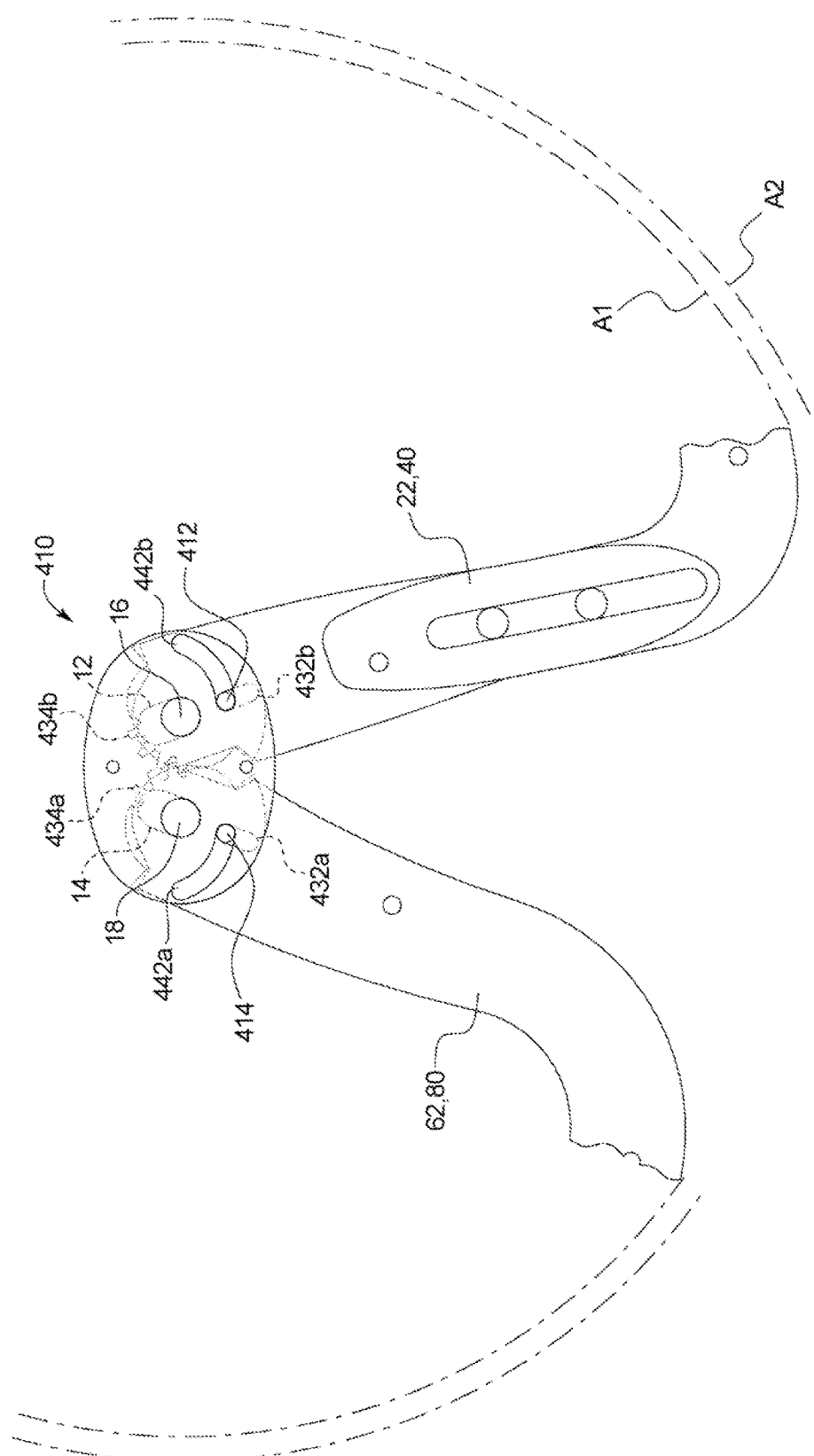

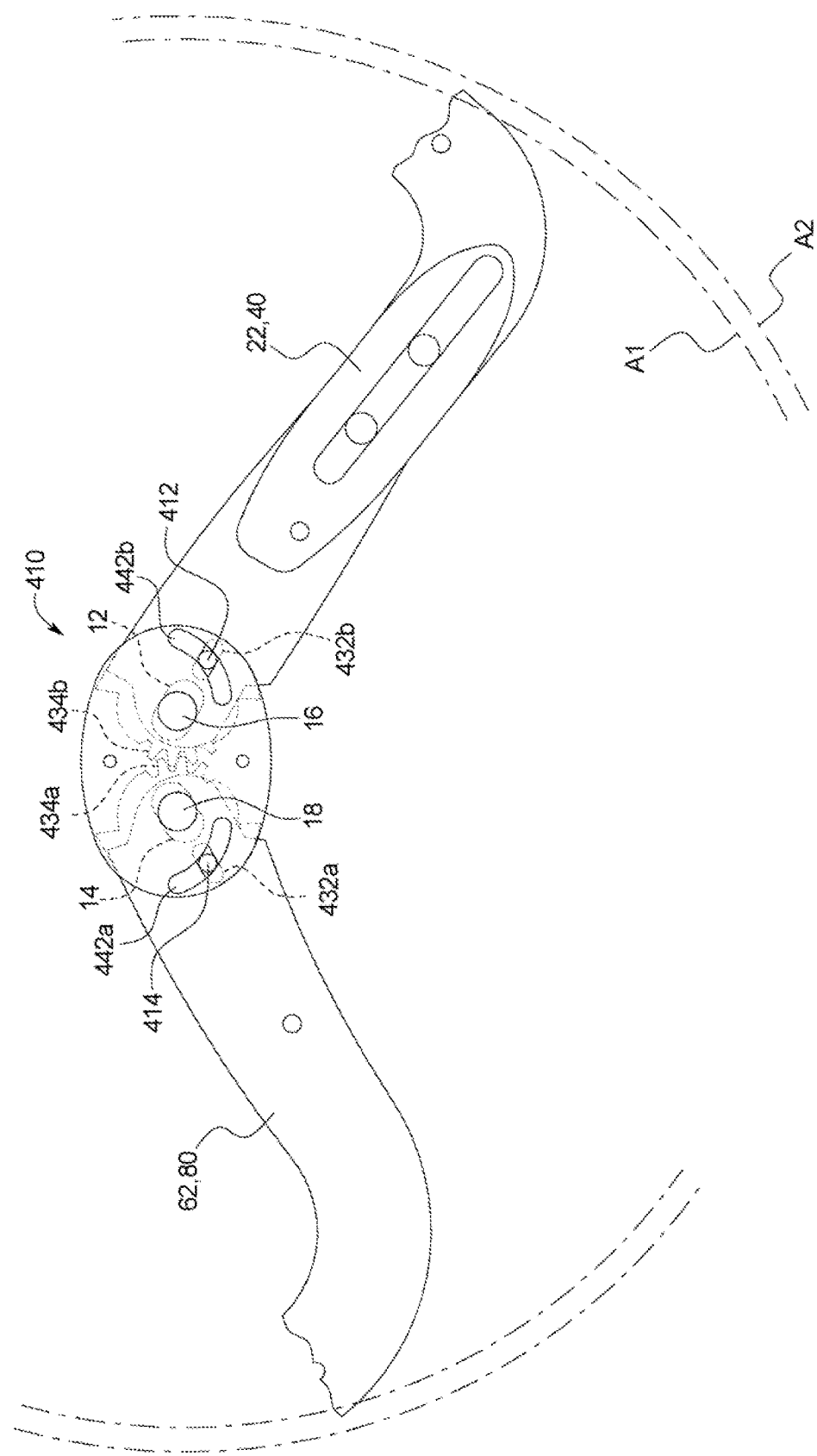

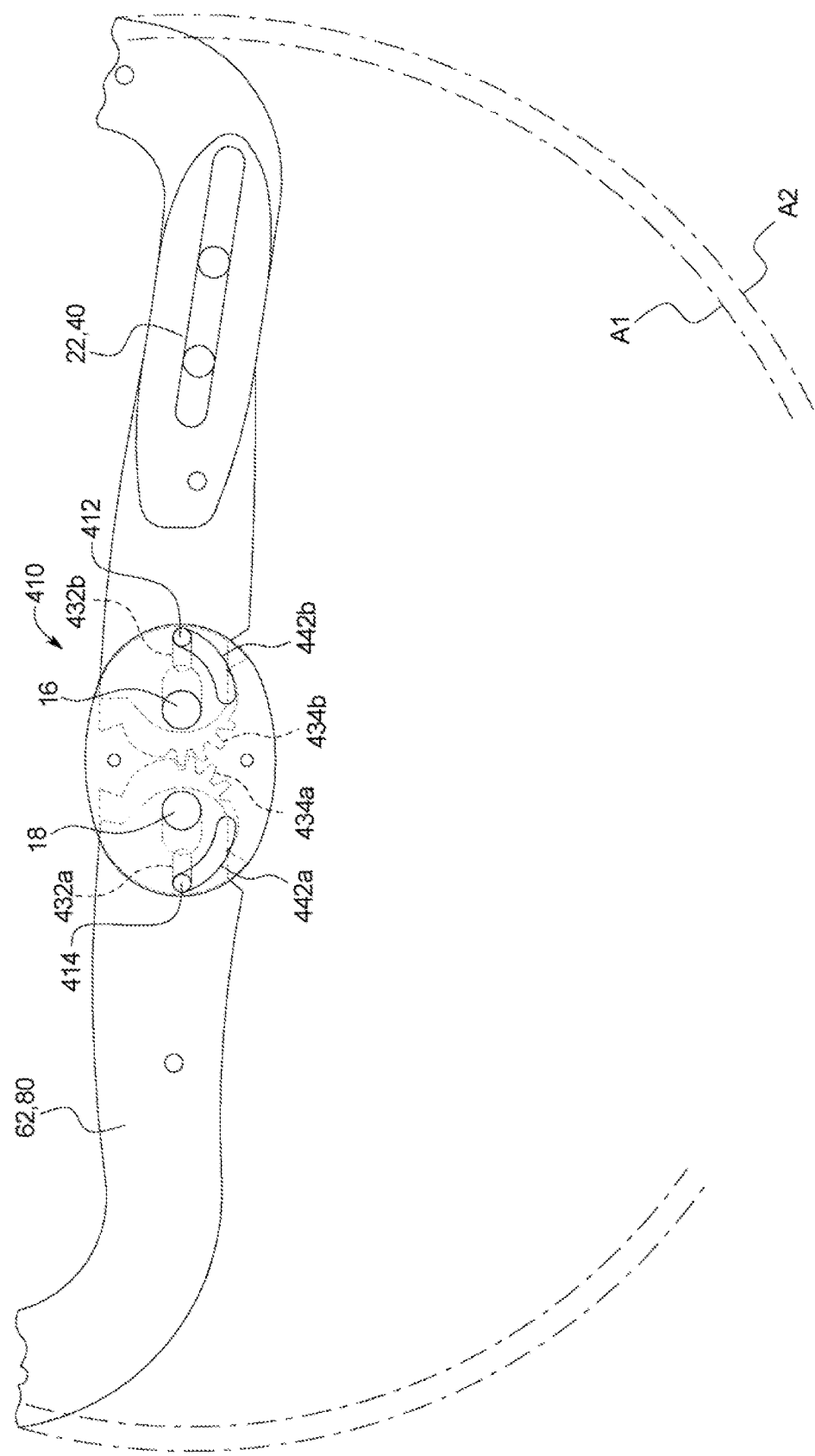

ORTHOPEDIC KNEE BRACE WITH DYNAMICALLY CHANGING MEDIAL AND LATERAL HINGES

BACKGROUND

The present disclosure relates to orthopedics generally and in particular to orthopedic knee braces.

Knee braces that attempt to provide beneficial side loads exist. Certain of these knee braces use pre-formed or pre-adjusted static angulation to create a side load at full extension. But the pre-formed or pre-adjusted static angulation causes the braces to roll circumferentially around the user's leg. Usually, the greater the pre-set angulation, the greater the rolling effect.

A need accordingly exists for an improved side load providing orthopedic knee brace.

SUMMARY

The present disclosure sets forth a dynamic double-upright Osteoarthritis ("OA") functional brace, which includes a pair of hinges and uprights located on either side of the user's leg. In particular, the brace includes an upper shell having medial and lateral uprights that extend upwardly from medial and lateral hinges, respectively, and meet along the front of the user's thigh. The brace includes a lower shell having medial and lateral uprights that extend downwardly from the medial and lateral hinges, respectively, and meet along the front of the user's knee. The shells can be made from many materials provided that the material is not so flexible that the material negates the loading features discussed below. The shells can for example be made of hard plastic or metal, such as steel, aluminum, magnesium and combinations or alloys thereof.

Each of the upper and lower shells supports straps that secure the upper shell to the user's thigh and the lower shell to the user's calf. The straps begin from hinged pivot points secured, for example, on the insides of the lateral uprights and extend through hinged loops secured, for example, secured to the outsides of the medial uprights. The user tensions the straps to a desired level and secures each strap to itself, for example, through the use of hook and pile connections. The straps can each have one or more foam pad for patient comfort secured again via hook and pile connections. While the shells extend around the front of the user's leg in one embodiment, it is contemplated to extend the straps both around the back and front of the user's leg. In one implementation, the upper and lower shells generally define the top and bottom of the brace, two intermediate straps extend around the front of the user's thigh and calf, respectively, and four straps extend around the back of the user's leg, aligning generally with the two shells and two frontwardly extending straps.

It is contemplated to allow one or both of the upwardly extending uprights to be adjustable in length. For example, the lateral upwardly extending upright can be made of two pieces, an inside piece extending from the lateral hinge and an outside piece slidingly engaging the outside of the inside piece and extending over to the medial hinge. The inside piece includes an elongated slot. The outside piece includes multiple fastener receiving apertures. Fasteners can be inserted from the inside of the inside upright piece, though the elongated slot of the inside upright piece, through the apertures of the outside upright piece, receiving nuts on the outside of the outside upright piece to tighten the outside upright piece to the inside piece at a desired relative location. Padding can be located to cover or obscure the screws on the inside of the brace, so that the user does not feel the screw heads. The adjustable length of the one or both upper uprights works in combination with the hinges to provide a desired dynamic side loading for the brace.

The hinges are configured and arranged to dynamically change the brace's medial and lateral angle as the brace moves through its range of motion from flexion to extension and vice versa. To accomplish this, in one embodiment one hinge (medial or lateral) extends in length, while the other hinge (lateral or medial) contracts in length as the brace moves from flexion (bent) to extension (unbent or straight). This dynamic feature advantageously applies a side force to the leg during extension and removes the side force during flexion. Removing the force during the flexion cycle allows more total force to be allowed or tolerated at extension and helps to prevent the brace from rolling circumferentially around the leg. The absence of force at flexion is also more comfortable to the wearer when not moving and seated, so that the user readily tolerates the brace.

The static length adjustment on at least one of the upright thigh arms mentioned above allows the user to add additional total angle to the brace at extension. The adjustment also allows the user to reduce the total angle if the user feels that the dynamic throw is too great. The brace could also be built with static adjustments in both upper uprights or thigh arms instead of just one.

The dynamic hinges in one embodiment use two four-bar linkages, wherein the medial and lateral hinges are configured differently in such a way that one hinge extends in overall length and the other hinge contracts in overall length, which provides the beneficial dynamic side loading action as the brace moves through its range of motion. Again, in one preferred embodiment, as the knee is extended load is applied. And when the knee is flexed the load is removed.

The insides and outsides of the hinge linkages are covered by one or more covering plate. The covering plates encapsulate the four bar linkages to prevent fingers or other objects from being caught in the scissor-like linkages. The four-bar hinge pivot members glide in slots formed on the insides of the hinge plates to allow the hinge plates to passively mimic the action of a polycentric knee hinge. The hinge plates cover the four-bar linkages, making the linkages safer while also allowing an attachment area on the insides of the hinges for padding and an attachment area on the outsides of the hinges to display logos, directions, setting information and the like. If desired, however, the four-bar hinges could be used alone, without the covering hinge plates.

Also, while in one preferred embodiment, both hinges change in length, one lengthening while the other shortening, it is possible that only one hinge lengthens or shortens, while the other hinge is a non-length-changing hinge. Further, the shells can extend across the users leg directly from the hinges (e.g., be attached to the rigid uprights) or extend across the user's leg at any point along the length of the upright (instead of at the top and bottom of the uprights as mentioned above and illustrated in detail below).

Still further alternatively, the brace can use other types of hinge linkages than four-bar linkages, such as a polycentric or a single pivot hinge, which like the four-bar linkages cause an overall lengthening or shortening of their connecting components. For example, and as alluded to above, the lengthening and shortening could alternatively be accomplished with a single extending hinge or a single contracting hinge on one (medial or lateral) side paired with a hinge on the other side (lateral or medial) of the brace that does not contract or extend, provided that the combination results in a differential change in length between the two hinges. The dynamic feature could alternatively be accomplished using a single extending hinge attached to upper and lower upright arms and two crisscrossing straps (one starting from each upright) that cross the knee opposite the side with the hinge and spiral in opposite directions, extending and attaching to the top or bottom of the opposing upright.

Although providing only a single extending or contracting linkage paired with a non-changing linkage may be suitable, it is believed that providing both an extending hinge and a contracting hinge may be the preferred and most efficient configuration because the configuration allows both hinges to be of the same size or similar in size and allows the hinges physically smaller. To that end, the bracing concept works with many brace sizes but may be most efficiently applied to smaller braces due to the hinges being in closer proximity to each other, which increases the overall angulation.

The brace may be used in one primary implementation for unicompartmental OA, but may also be used to unload pressure on a tibial osteotomy or to unload a ligament or meniscus injury or repair. It is envisioned to use the brace in any type of bracing situation that can benefit from the dynamic side angulation of a joint moving within its normal range of motion, including functional hard frame braces, soft neoprene type braces and post-operative braces.

It is accordingly an advantage of the present disclosure to provide an orthopedic knee brace that applies a dynamic side load in extension but removes the load during flexion.

It is another advantage of the present disclosure to provide an orthopedic knee brace that increases user comfort.

It is a further advantage of the present disclosure to provide an orthopedic knee brace that reduces a tendency for the brace to roll circumferentially about the user's leg.

It is yet another advantage of the present disclosure to provide a dynamic orthopedic knee brace that is easy to apply manipulate and remove.

Additional features and advantages are described herein, and will be apparent from the following Detailed Description and the figures.

BRIEF DESCRIPTION OF THE FIGURES

FIGS. 5A to 5C are side elevation views of one embodiment of the hinge and its associated linkage that shortens or contracts in overall length as the brace moves from total flexion (FIG. 5A) to a rotational midpoint (FIG. 5B) to total extension (FIG. 5C).

FIGS. 6A to 6C are side elevation views of one embodiment of the hinge and its associated linkage that lengthens or expands in overall length as the brace moves from total flexion (FIG. 6A) to a rotational midpoint (FIG. 6B) to total extension (FIG. 6C).

FIGS. 7A to 7C are lateral, front and medial elevation views, respectively, of one embodiment of the dynamically changing orthopedic knee brace of the present disclosure being worn by a user during mid-stride, showing the resulting force vectors.

FIGS. 8A to 8C are lateral, front and medial elevation views, respectively, of one embodiment of the dynamically changing orthopedic knee brace of the present disclosure being worn by a user at full stride extension, showing the resulting force vectors.

FIGS. 11A to 11C are side elevation views of the hinge of FIG. 9 and its associated linkage that shortens or contracts in overall length as the brace moves from total flexion (FIG. 11A) to a rotational midpoint (FIG. 11B) to total extension (FIG. 11C).

FIGS. 12A to 12C are side elevation views of the hinge of FIG. 10 and its associated linkage that lengthens or expands in overall length as the brace moves from total flexion (FIG. 12A) to a rotational midpoint (FIG. 12B) to total extension (FIG. 12C).

DETAILED DESCRIPTION

Brace Generally

Figure 1:
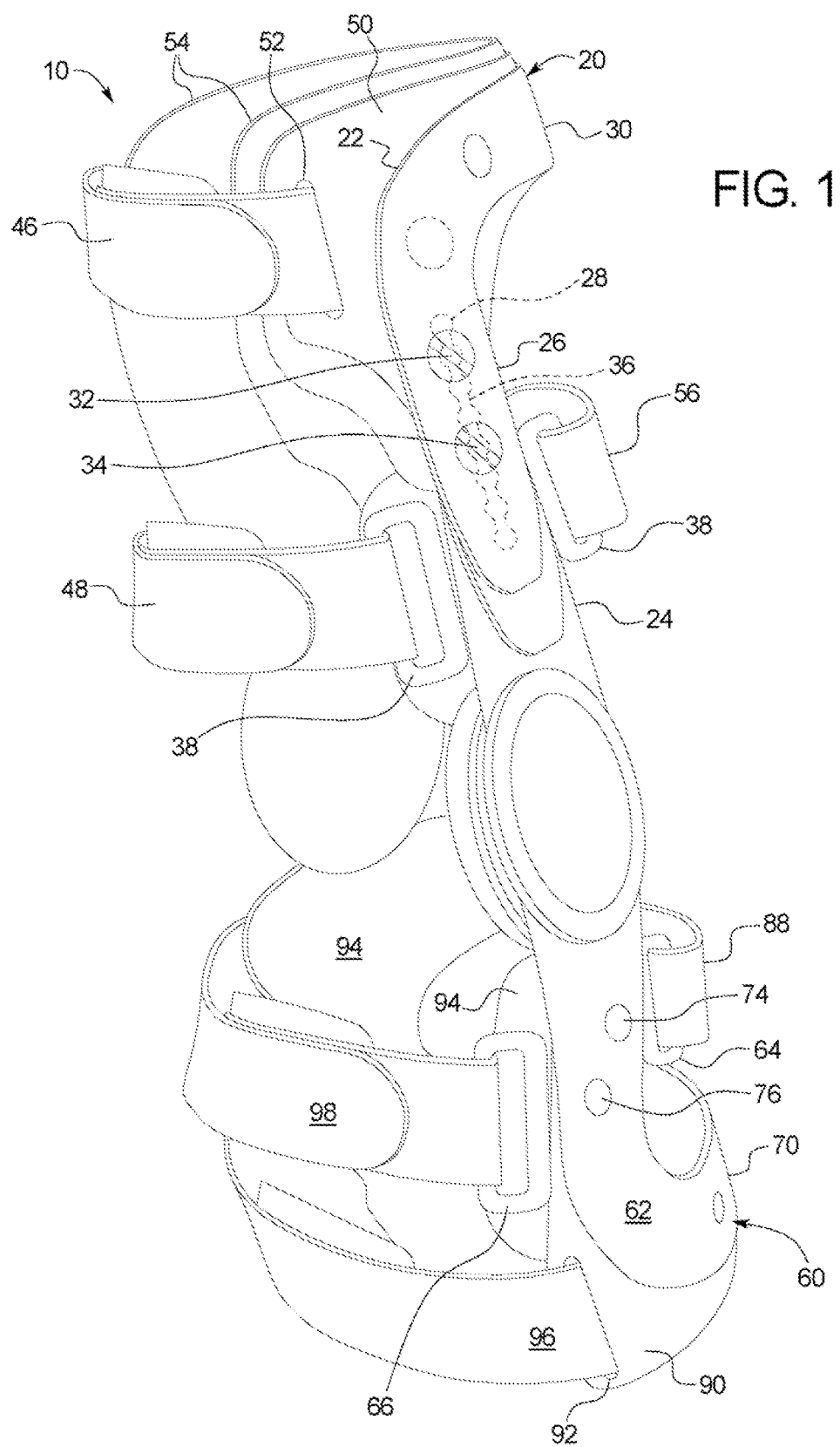
FIG. 1 is a perspective view of one embodiment of the dynamically changing orthopedic knee brace of the present disclosure.
Figure 2:
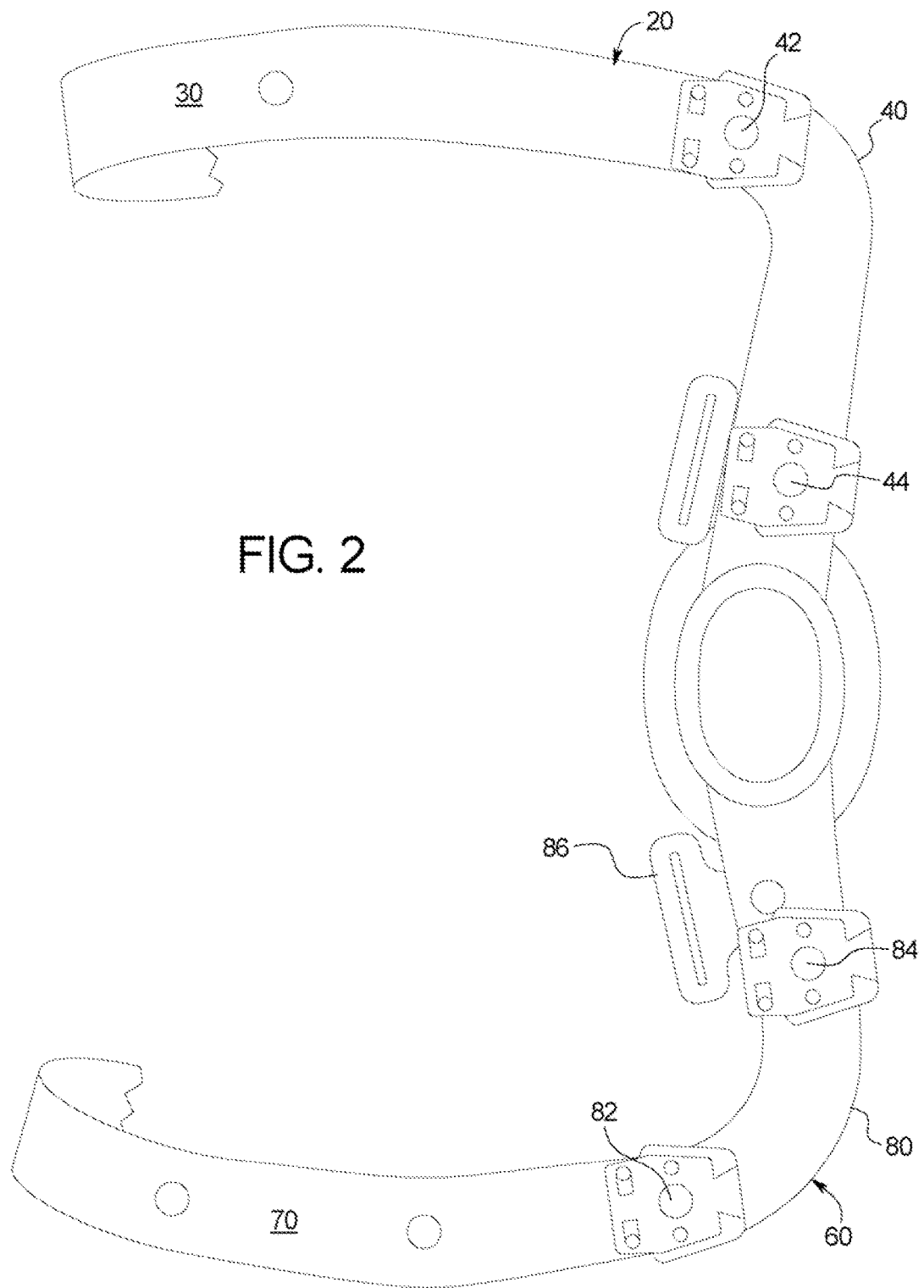
FIG. 2 illustrates an embodiment of the medial hinge and medial upper and lower uprights extending from the medial hinge from the outside, the side not seen in FIG. 1

Referring now to the drawings and in particular to FIGS. 1 and 2, one embodiment of a dynamically changing orthopedic knee brace of the present disclosure is illustrated by brace 10. Brace 10 includes an upper shell 20 and a lower shell 60. Upper and lower shells 20 and 60 can be made of rigid plastic, a composite material, metal and/or any combination thereof. Aluminum, magnesium, steel, combinations and alloys thereof may be used for example. The shell material can be somewhat flexible but should not be so flexible that that the material negates the dynamic loading features discussed herein.

Upper shell 20 includes an upper lateral upright 22 and an upper medial upright 40. Uprights 22 and 40 may extend into each other at shell front 30 forming a continuous shell as illustrated or terminate at separate ends. Shell front 30 is shown extending from the top of lateral upright 22 to the top of medial upright 40 but can alternatively extend from a lower point along one or both of lateral upright 22 and medial upright 40. In another alternative embodiment, shell front 30 extends directly from one or both of the lateral or medial hinges discussed in detail below.

As illustrated in FIG. 1, upper lateral upright 22 includes an inner piece 24 and an outer piece 26. Inner piece 24 slideably and adjustably engages outer piece 26. Inner piece 24 includes a lower end that forms part of the lateral hinge. Outer piece 26 extends into shell front 30, which in turn extends into upper medial upright 40, which terminates as part of the medial hinge. To this end, inner piece 24 includes or defines an elongated slot 28 (shown in phantom because it is hidden behind outer piece 26). Outer piece 26 in turn includes or defines mounting holes 32 and 34, which are centered to both align with slot 28. Screws are inserted from the inside out in one embodiment, so as to extend from the inside wall of inner piece 24, through slot 28, and through one of mounting holes 32 and 34, and to receive a nut on the outside wall of outer piece 26. Padding can be provided on the inner wall of one or both of inner piece 24 and outer piece 26 (where exposed) to hide or obscure the screw head so that the user does not feel the screw.

The nuts covering holes 32 and 34 as shown in FIG. 1 can each have a slot that receives a flathead screw driver or other instrument for loosening and tightening the screw and nut. In this manner, the user can easily adjust the height of outer piece 26 relative to inner piece 24 once, such that the setting will remain until the user changes the setting. To this end, slot 28 can have side serrations 36 as illustrated to help lock the mounting screws into desired vertical locations along slot 28.

As discussed below, the lengthening of one hinge (210 below) and the shortening of the opposite hinge (110 below) changes the overall angle of the brace, as viewed from the front (see FIGS. 7A to 8C below), as if brace 10 is being bent sideways analogous to a boomerang. The sideways bending of brace 10 creates a sideways bending force on the leg as a pair of shields (50 and 90 at the top and bottom, respectively, of brace 10 discussed below) load one side of the user's knee and are opposed by the inside face of the opposing hinge (e.g., via hinge 110, which is cushioned with a foam pad in one preferred embodiment), which serves as a fulcrum. Pulling outer piece 26 of upper lateral upright 22 upward relative to inner piece 24 of upper lateral upright 22 past a natural or unloaded position will tend to increase the overall sideways angle of brace 10, increasing the overall sideways bending force provided by the hinges. On the other hand, pushing outer piece 26 of upper lateral upright 22 downward relative to inner piece 24 of upper lateral upright 22 past the natural or unloaded position will decrease the overall sideways angle of brace 10, decreasing the overall sideways bending force provided by the hinges.

If needed, the same type of sliding adjustability can be provided alternatively or additionally along upper medial upright 40. Changes such as not providing serrations 36, forming the slot in outer piece 26 and the mounting holes 32 and 34 in inner piece 24, and/or changing the mounting direction of the screws, and/or threading or providing threaded inserts in one of the inner and outer pieces instead of using external nuts, are within the scope of the present disclosure.

Hidden from view in FIG. 1 is a rotatably mounted pin in inner piece 24 to which strap holding ring connectors 38 are fastened. The rotatably mounted pin allows ring connectors 38 to rotate up and down relative to inner piece 24 of upper lateral upright 22. A tough, e.g., polyethylene, flexible plastic shield 50 is riveted bolted or otherwise secured to shell front 30. Plastic shield 50 allows for cost and weight to be reduced. Shield 50 defines a strap receiving aperture 52. Shield 50 also provides a larger surface area for releasable securing a large foam pad 54, e.g., via hook and pile connection. As illustrated in FIG. 2, an upper strap ring connector 42 and an intermediate strap ring connector 44 are connected rotatably to upper medial upright 40, so as to be able to rotate up and down relative to upper medial upright 40 in the same manner as strap holding ring connectors 38 relative to upper lateral upright 22.

In the illustrated embodiment, an upper rearwardly extending strap 46 begins via a looped end extending through strap receiving aperture 52 of shield 50, extends around a back of the user's thigh, loops through upper strap loop connector 42 of upper medial upright 40 and folds back over itself for adjustable fastening at a user desired tension via hook and pile connection. An intermediate rearwardly extending strap 48 begins via a looped end extending through strap receiving connector 38 featured rotatably to inner piece 24, extends around a lower portion of the back of the user's thigh, loops through intermediate strap connecting loop 44 of upper medial upright 40 and folds back over itself for adjustable fastening at a user desired tension via hook and pile connection. A third strap 56 begins via a looped end extending through strap receiving connector 38 featured rotatably to inner piece 24, extends around a lower portion of the front of the user's thigh, loops through intermediate strap connecting loop 44 (shown in FIG. 2 as single-ended but is actually double-ended to loop both rear strap 48 and front strap 56) of upper medial upright 40 and folds back over itself for adjustable fastening at a user desired tension via hook and pile connection. Upper, rearwardly extending strap 46 is generally aligned with shell front 30, while intermediate, rearwardly extending strap 48 is generally aligned with intermediate, forwardly extending strap 56.

Lower shell 60 includes a lower lateral upright 62 and a lower medial upright 80. Uprights 62 and 80 may extend into each other at shell front 70 forming a continuous shell as illustrated or terminate at separate ends. Shell front 70 is shown extending from the bottom of lower lateral upright 62 to the bottom of lower medial upright 80 but can alternatively extend from a higher point along one or both of lateral upright 62 and medial upright 80. In another alternative embodiment, shell front 70 extends directly from one or both of the lateral or medial hinges. In still a further alternative embodiment, either one or both of upper shell front 30 and/or lower shell front 70 could alternatively wrap around the back of the user's leg. The associated respective upper and lower straps 46 and 96 could then instead wrap around the front of the user's leg.

The static, linear adjustment of inner piece 24 of upper lateral upright 22 relative to inner piece 26 of upper lateral upright 22 may be applied alternatively or additionally to either one or both of lower lateral upright 62 and lower medial upright 80. All alternatives discussed above for the static, linear adjustment are equally applicable to an application of same lower lateral upright 62 and/or lower medial upright 80.

As illustrated in FIG. 1, strap holding ring connectors 64 and 66 are fastened rotatably to lower lateral upright 62 via respective mounting pins 74 and 76. Mounting pins 74 and 76 allow ring connectors 64 and 66 to rotate up and down relative to lower lateral upright 62. A second tough, e.g., polyethylene, flexible plastic shield 90 is riveted, bolted or otherwise secured to lower shell front 70. Plastic shield 90 also allows for cost and weight to be reduced, defines a strap receiving aperture 92, and provides a larger surface area for releasable securing a lower foam pad 94, e.g., via hook and pile connection. In one embodiment plastic shields 50 and 90 are used only on the side of brace 10 having lengthening hinge 210 discussed in detail below, whether used as the lateral or medial hinge.

As illustrated in FIG. 2, a lower strap connecting loop 82 and two intermediate strap connecting loops 84 and 86 are connected rotatably to lower medial upright 80, so as to be able to rotate up and down relative to the lower medial upright in the same manner as strap holding ring connectors 64 and 66 relative to lower lateral upright 62.

In the illustrated embodiment, a lower rearwardly extending strap 96 begins via a looped end extending through strap receiving aperture 92 of plastic shield 90, extends around a back of the user's calf, loops through lower strap connecting loop 82 of lower medial upright 80 and folds back over itself for adjustable fastening at a user desired tension via hook and pile connection. An intermediate rearwardly extending strap 98 begins via a looped end extending through strap receiving connector 66 fastened rotatably to lower lateral upright 62, extends around an upper portion of the back of the user's calf, loops through intermediate strap connecting loop 84 of lower medial upright 80 and folds back over itself for adjustable fastening at a user desired tension via hook and pile connection. A third strap 88 begins via a looped end extending through strap receiving connector 64 fastened rotatably to lower lateral upright 62, extends around an upper portion of the front of the user's calf, loops through intermediate strap connecting loop 86 of lower medial upright 80 and folds back over itself for adjustable fastening at a user desired tension via hook and pile connection. Lower, rearwardly extending strap 96 is generally aligned with lower shell front 70, while intermediate, rearwardly extending strap 98 is generally aligned with intermediate, forwardly extending strap 88.

Any of the straps discussed herein can be elastic or relatively non-stretchable. The straps can be made of a nylon webbing for example and have hook or pile material for releasably securing foam padding in desired places.

Dynamically Changing Hinges

Figure 3:
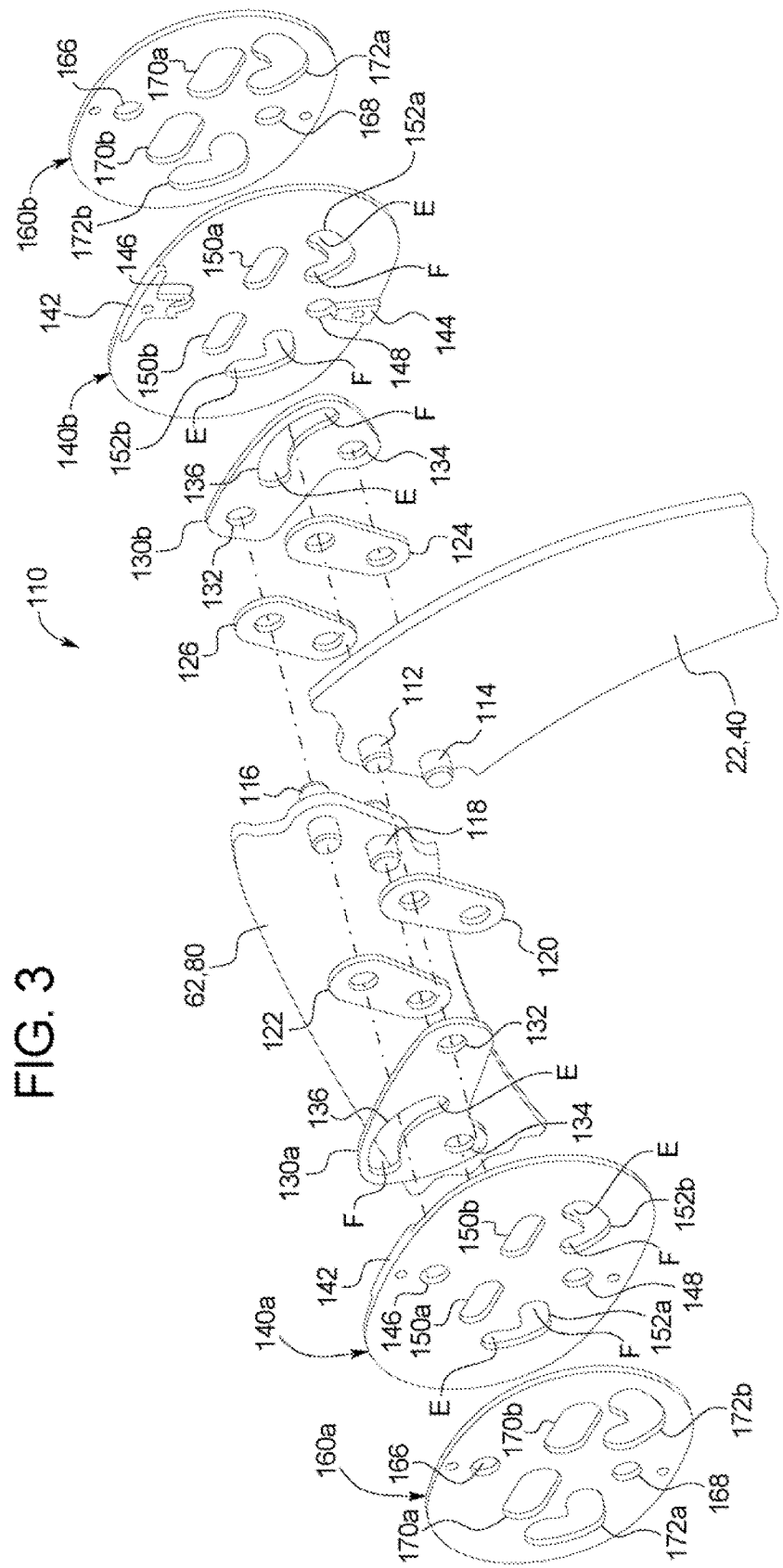
FIG. 3 is an exploded perspective view of one embodiment of a hinge that shortens or contracts in overall length as the brace moves from flexion to extension (bent position to extended position).

FIG. 1 illustrates a lateral hinge for brace 10, while FIG. 2 illustrates a medial hinge for brace 10. FIG. 3 illustrates one embodiment for a hinge 110 that shortens or contracts in overall vertical length as brace 10 moves from flexion to extension (bent leg position to extended leg position). Depending upon the user's condition, hinge 110 can be used as the lateral hinge for brace 10 shown in FIG. 1 or as the medial hinge for brace 10 shown in FIG. 2.

FIG. 3 illustrates that upper lateral upright 22 and upper medial upright 40 can each be fitted or formed with an upper primary pin 112 and an upper support pin 114. Pins 112 and 114 extend through to both sides of upper lateral upright 22 and upper medial upright 40 in one embodiment (only one side can be seen in the perspective view of FIG. 3). Pins 112 and 114 can be hard steel or stainless steel and can be inserted (e.g., press-fit) though mating holes formed in upper lateral upright 22 and upper medial upright 40, after which pins 112 and 114 are welded or glued into place. Alternatively, pins 112 and 114 are machined along with upper lateral upright 22 and upper medial upright 40.

FIG. 3 also illustrates that lower lateral upright 62 and lower medial upright 80 can each be fitted or formed with a lower primary pin 116 and a lower support pin 118. Pins 116 and 118 again in an embodiment extend through to both sides of lower lateral upright 62 and lower medial upright 80 (pins can be seen on both sides the perspective view of FIG. 3). Pins 116 and 118 can again be hard steel or stainless steel and can be inserted (e.g., press-fit) though mating holes formed in lower lateral upright 62 and lower medial upright 80, after which pins 116 and 118 are welded or glued into place. Alternatively, pins 116 and 118 are machined along with lower lateral upright 62 and lower medial upright 80.

In the illustrated embodiment, each side of each upright is fitted with a wear or rubbing plate, which likewise can be made of a hard metal, such as steel or stainless steel. The hard metal wear or rubbing plates can be welded or glued to the uprights. The wear or rubbing plates are alternatively made of a tough plastic, such as teflon, which can be glued to the uprights or fitted replaceably onto the uprights.

In the illustrated embodiment, wear or rubbing plate 120 fits over upper primary pin 112 and upper support pin 114 and onto the viewable side of upper lateral upright 22 or upper medial upright 40 in FIG. 3. Wear or rubbing plate 122 fits over lower primary pin 116 and lower support pin 118 and onto the viewable side of lower lateral upright 62 or lower medial upright 80 in FIG. 3. Wear or rubbing plate 124 fits over upper primary pin 112 and upper support pin 114 and onto the non-viewable side of upper lateral upright 22 or upper medial upright 40 in FIG. 3. Wear or rubbing plate 126 fits over lower primary pin 116 and lower support pin 118 and onto the non-viewable side of lower lateral upright 62 or lower medial upright 80 in FIG. 3.

As discussed herein, the hinges of the present disclosure are four-bar hinges in one embodiment. The two uprights connected to each hinge provide two of the four bars of the linkages. With hinge 110, the other two bars of the four bars are provided by linkage members 130*a* and 130*b*. As illustrated in FIG. 3, linkage member 130*a* is mounted on the viewable sides of the uprights against the associated wear or rubbing plates 120 and 122, while linkage member 130*b* is flipped relative to linkage member 130*a* and is mounted on the non-viewable sides of the uprights against the associated wear or rubbing plates 124 and 126.

Linkage members 130*a* and 130*b* are made of hard metal in one embodiment, such as steel or stainless steel. Each linkage member 130*a* and 130*b* includes or forms a primary aperture 132, a support aperture 134 and a primary slot 136. On the viewable side of the uprights, primary aperture 132 of linkage member 130*a* is in rotatable communication with upper primary pin 112. Support aperture 134 of linkage member 130*a* is in rotatable communication with lower support pin 118. Primary slot 136 of linkage member 130*a* is in curving and sliding communication with lower primary pin 116. Upper support pin 114 does not communicate with linkage member 130*a*.

On the non-viewable side of the uprights, primary aperture 132 of linkage member 130*b* is in rotatable communication with lower primary pin 116. Support aperture 134 of linkage member 130*b* is in rotatable communication with upper support pin 114. Primary slot 136 of linkage member 130*b* is in curving and sliding communication with upper primary pin 112. Lower support pin 118 does not communicate with linkage member 130*b*.

If one imagines linkage members 130*a* and 130*b* placed onto pins 112, 114, 116 and 118 and the upper upright 22, 40 being pulled away from the lower upright 62, 80, e.g., from a flexion or bent knee position to an extended or unbent knee position, it should become apparent that the primary apertures 132 and support apertures 134 will control how upper upright 22, 40 will move and rotate relative to lower upright 62, 80 because the circular apertures leave no room for the corresponding and interacting pins to move relative to each other. The distance and relative positioning between primary aperture 132 and support aperture 134 is fixed. The pins that extend through primary slots 136 are in essence along for the ride.

Primary slots 136 have been marked with a flexion end F and an extension end E. When brace 10 is in the totally flexed or flexion position, primary pins 112 and 116 reside on the flexion ends F of slots 136. As brace 10 opens up, primary pins 112 and 116 slide along slots 136 towards extension ends E and eventually reach extension ends E when brace 10 is fully extended or unbent. While slots 136 would appear to make the primary pins 112 and 116 travel towards each other in a curved or arced manner, the relative travel of primary pins 112 and 116 towards each is actually linear in general. This shortening of linear distance between primary pins 112 and 116 corresponds to, or is the reason why, upper upright 22, 40 and lower upright 62, 80 strike a decreasing arc when traveling from flexion to extension as shown in FIGS. 5A to 5C.

Hinge 110 could operate with the apparatus just described, that is, without cover plates. In one preferred embodiment, however, the uprights are covered at the hinged ends on each side by at least one cover plate. The cover plates protect the user from the potentially pinching action of linkage members 130a and 130b and pins 112, 114, 116 and 118. The cover plates also provide the hinges with areas to attach needed external items, such as padding (e.g., on the inside of hinge 110), logos, instructions and setting information (e.g., on the outside of hinge 110).

In the illustrated embodiment, each side of upper upright 22, 40 and lower upright 62, 80 is covered by an inner cover plate 140a, 140b and a corresponding outer cover plate 160a, 160b. Inner cover plates 140a and 140b can be plastic or metal, e.g., nylon, steel, stainless steel or aluminum. Inner cover plates 140a and 140b include formed or attached raised portions 142 and 144. Raised portions 142 and 144 leave thinner or non-raised areas of the inner cover plates 140a and 140b that are open to receive the linkage members 130a and 130b though their entire range of motion. In an embodiment, raised portions 142 and 144 are raised so as to have a thickness the same as or slightly greater than the thickness of linkage members 130a and 130b. The inside surfaces of raised portions 142 and 144 are thus set off from the outside surfaces of uprights 22, 40 and 62, 80 by a thickness equal to or slightly less than the thickness of wear or rubbing plates 120, 122, 124 and 126, such that the uprights are free from rubbing contact with inner cover plates 140a and 140b.

Inner cover plates 140a and 140b include or define fastener receiving holes 146 and 148 for receiving rivets, bolts, barbs and the like for securing together the assembled hinge 110. Inner cover plates 140a and 140b also include or define pin receiving slots and in particular primary pin receiving slots 150a and 150b and support pin receiving slots 152a and 152b. The shapes of the pin receiving slots confirm the relative motion of primary pins 112 and 116 discussed above and show how support pins 114 and 118 move relative to each other.

Primary pin receiving slots 150a and 150b confirm that primary pins 112 and 116 move generally linearly towards each other from flexion to extension. The length of each slot 150a and 150b is the same and is indicative of the distance that the arc struck by uprights 22, 40 and 62, 80 contracts over the course of moving from total flexion to total extension.

Support pin slots 152a and 152b have been marked on their ends with a flexion F and an extension E as has been done with slots 136 of linkage members 130a and 130b to show the movement of support pins 114 and 118 both alone and in relation to each other. Unlike primary pins 112 and 116, support pins 114 and 118 move generally away from each other when brace 10 is rotated from flexion F to extension E. Also unlike primary pins 112 and 116, which move linearly towards each other, support pins 114 and 118 move away from each other but do so by sweeping through the illustrated curves or arcs.

Outer cover plates 160a and 160b can be a tough plastic or metal, e.g., full-hardened stainless steel or full-hardened steel, and can be roughened so as to be readily secured adhesively to a hook or pile material. The hook or pile material receives mating pile or hook material on a final removable and replaceable solid cover, such as a foam pad cover (not illustrated) on the inside of hinge 110 and a solid logo, instruction and/or setting information bearing cover located on the outside of hinge 110. Outer cover plates 160a and 160b include fastener receiving holes 166 and 168, primary pin receiving slots 170a and 170b and support pin slots 172a and 172b, which in general serve the same purpose as the counterpart holes and slots formed in inner cover plates 140a and 140b.

It should be appreciated that inner cover plates 140a and 140b could be made alternatively to be thick enough to cover the entire lengths of pins 112, 114, 116 and 118, such that outer cover plates 160a and 160b do not need primary pin receiving slots 170a and 170b and support pin slots 172a and 172b. In any case, for safety and operational reasons, it is preferred to not allow to pins 112, 114, 116 and 118 or linkage members 130a and 130b to be exposed or viewed, where they could hurt the user or another person and/or become damaged or obstructed.

Figure 4:
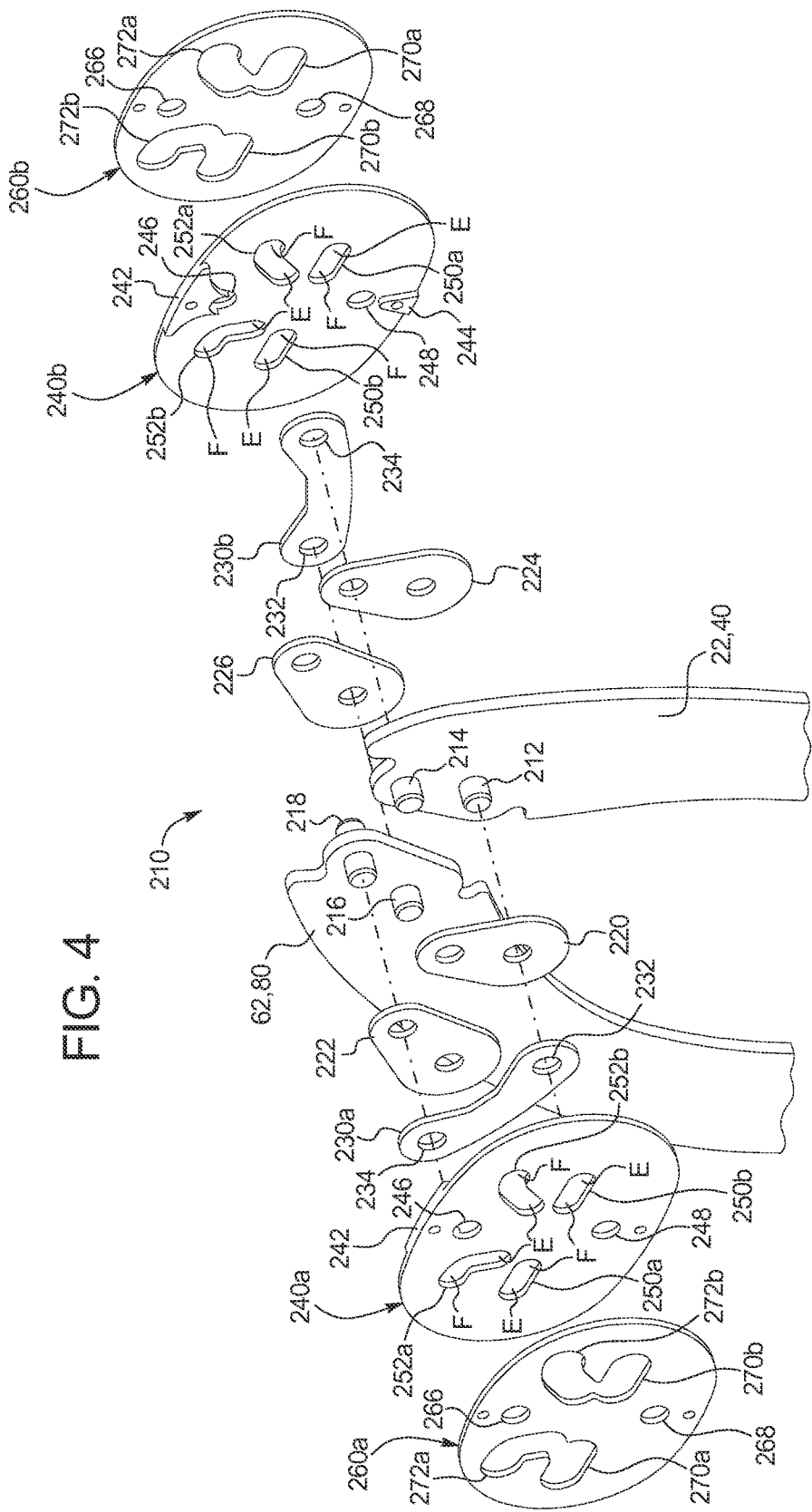
FIG. 4 is an exploded perspective view of one embodiment of a hinge that lengthens or expands in overall length as the brace moves from flexion to extension (bent position to extended position).

Referring now to FIG. 4, one embodiment for a hinge 210 that lengthens or expands in overall vertical length as brace 10 moves from flexion to extension (bent position to extended position) is illustrated. As with hinge 110, depending upon the user's condition, hinge 210 can be provided as the lateral hinge for brace 10 shown in FIG. 1 or as the medial hinge for brace 10 shown in FIG. 2. In one preferred embodiment however, hinge 210 is provided on the medial or lateral side of the brace, while hinge 110 is provided on the respective opposite side of brace 10.

FIG. 4 illustrates that upper lateral upright 22 and upper medial upright 40 can each be fitted or formed with an upper primary pin 212 and an upper support pin 214 (primary pin 212 is located below support pin 214 in FIG. 4 as opposed to corresponding pins 112 and 114 above in FIG. 3). Pins 212 and 214 extend through to both sides of upper lateral upright 22 and upper medial upright 40 in one embodiment and can be of any material and formed in any way discussed above for pins 112 and 114.

FIG. 4 also illustrates that lower lateral upright 62 and lower medial upright 80 can each be fitted or formed with a lower primary pin 216 and a lower support pin 218 (primary pin 216 is located below support pin 218 in FIG. 4 as opposed to corresponding pins 116 and 118 above in FIG. 3). Pins 216 and 218 extend through to both sides of lower lateral upright 62 and lower medial upright 80 in one embodiment and can be of any material and formed in any way discussed above for pins 116 and 118.

Each side of each upright is again fitted with a wear or rubbing plate, which can be made of any of the materials discussed above for rubbing plates 120, 122, 124 and 126. As illustrated, wear or rubbing plate 220 fits over upper primary pin 212 and upper support pin 214 and onto the viewable side of upper lateral upright 22 or upper medial upright 40 in FIG. 4. Wear or rubbing plate 222 his over lower primary pin 216 and lower support pin 218 and onto the viewable side of lower lateral upright 62 or lower medial upright 80 in FIG. 4. Wear or rubbing plate 224 fits over upper primary pin 212 and upper support pin 214 and onto the non-viewable side of upper lateral upright 22 or upper medial upright 40 in FIG. 4. Wear or rubbing plate 226 fits over lower primary pin 216 and lower support pin 218 and onto the non-viewable side of lower lateral upright 62 or lower medial upright 80 in FIG. 4.

As with hinge 110, hinge 210 is a four-bar hinge in one embodiment, wherein the two uprights connected to hinge 210 provide two of the four bars of the linkages. With hinge 210, the other two bars of the four bars are provided by linkage members 230a and 230b. As illustrated in FIG. 4, linkage member 230a is mounted on the viewable sides of the uprights against the associated wear or rubbing plates 220 and 222, while linkage member 230b is flipped relative to linkage member 230a and is mounted on the non-viewable sides of the uprights against the associated wear or rubbing plates 224 and 226.

Linkage members 230a and 230b are made of any of the materials discussed above for linkage members 130a and 130b. Unlike linkage members 130a and 130b, however, each linkage member 230a and 230b is more of a straight, elongated member and includes or forms a primary aperture 232 and a support aperture 234 but no slot (like slot 136). On the viewable side of the uprights, primary aperture 232 of linkage member 230a is in rotatable communication with upper primary pin 212. Support aperture 234 of linkage member 230a is in rotatable communication with lower support pin 218. Upper support pin 214 and lower primary pin 216 do not communicate with linkage member 230a.

On the non-viewable side of the uprights, primary aperture 232 of linkage member 230b is in rotatable communication with lower primary pin 216. Support aperture 234 of linkage member 130b is in rotatable communication with upper support pin 214. Upper primary pin 212 and lower support pin 218 do not communicate with linkage member 230b.

The four-bar linkage of hinge 210 operates in the reverse of the four-bar linkage of hinge 110. If one imagines (i) linkage member 230a placed onto pins 212 and 218, (ii) linkage member 230b placed onto pins 214 and 216 and (iii) the upper upright 22, 40 being pulled away from the lower upright 62, 80, e.g., from a flexion or bent knee position to an extended or unbent knee position, it should appreciated the generally trapezoidal arrangement of pins 212, 214, 216 and 218 predisposes the scissor-like movement of linkage members 230a and 230b to cause the outer trapezoidal primary pins 212 and 216 to move horizontally outwardly in the view of FIG. 4 and the inner trapezoidal support pins 214 and 218 to move diagonally inwardly in the view of FIG. 4. Such relative movement may be helped via the slot arrangements discussed below for the cover plates.

In particular, hinge 210 could operate with the apparatus just described, that is, without cover plates. In one preferred embodiment, however, the uprights are covered at their hinged ends on each side by at least one cover plate, which can serve any of the purposes discussed above for cover plates 140a, 140b, 160a and 160b. In the illustrated embodiment, each side of upper upright 22, 40 and lower upright 62, 80 is covered by an inner cover plate 240a, 240b and a corresponding outer cover plate 260a, 260b. Inner cover plates 240a and 240b and outer cover plates 260a and 260b can be made of any of the materials discussed above for the cover plates of hinge 110.

Inner cover plates 240a and 240b again include formed or attached raised portions 242 and 244, which are formed via any of the methods discussed above and perform each of the functions discussed above for raised portions 142 and 144. Inner cover plates 240a and 240b also include or define fastener receiving holes 246 and 248 for receiving rivets, bolts, barbs and the like for securing the assembled hinge 210. Inner cover plates 240a and 240b further include or define pin receiving slots and in particular primary pin receiving slots 250a and 250b and support pin receiving slots 252a and 252b. The pin receiving slots illustrate the relative motion of primary pins 212 and 216 and support pins 214 and 218.

Primary pin receiving slots 250a and 250b have been marked with flexion F and an extension E to show the beginning and end of movement of primary pins 212 and 216 during an extension of brace 10. As illustrated, primary pins 212 and 216 move generally linearly away from each other when hinge 210 moves from flexion F to extension E. This lengthening of linear distance between primary pins 212 and 216 corresponds to, or is the reason why, upper upright 22, 40 and lower upright 62, 80 strike an increasing arc when traveling from flexion to extension as shown in FIGS. 6A to 6C. The length of each slot 250a and 250b is the same and is indicative of the distance over which arc struck by uprights 22, 40 and 62, 80 expands when brace 10 moves from total flexion to total extension.

Support pin slots 252a and 252b have likewise been marked on their ends with a flexion F and an extension E, as has been done with slots 250a and 250b, to show the movement of support pins 214 and 218 both alone and in relation to each other. Unlike primary pins 212 and 216, support pins 214 and 218 move generally towards each other when brace 10 is rotated from flexion F to extension E. Also unlike primary pins 212 and 216, which move generally linearly away from each other, support pins 214 and 218 move towards each other by sweeping through the illustrated curves or arcs.

Outer cover plates 260a and 260b can be roughened so as to be readily secured adhesively to a hook or pile material for reasons discussed above with outer cover plates 160a and 160b. Outer cover plates 260a and 260b include fastener receiving holes 266 and 268, primary pin receiving slots 270a and 270b and support pin slots 272a and 272b, which in general serve the same purpose as the counterpart holes and slots formed in inner cover plates 240a and 240b.

It should be appreciated that inner cover plates 240a and 240b could be made alternatively to be thick enough to cover the entire lengths of pins 212, 214, 216 and 218, such that outer cover plates 260a and 260b do not need primary pin receiving slots 270a and 270b and support pin slots 272a and 272b. As discussed above, for safety and operational reasons, it is preferred not to allow to pins 212, 214, 216 and 218 or linkage members 230a and 230b to be exposed or viewed, where they could hurt the user or another person and/or become damaged or obstructed.

Referring now to FIGS. 5A to 5C, hinge 110 is shown contracting in an overall arc length struck as upper upright 22, 40 and lower upright 62, 80 are rotated from total flexion (FIG. 5A), to a midpoint of rotation (FIG. 5B), to total extension (FIG. 5C). The locations of pins 112, 114, 116 and 118 are also shown in each snapshot. The broken lines indicate the largest arc A1 and the smallest arc A2 struck by upper upright 22, 40 and lower upright 62, 80.

In FIG. 5A (total flexion), primary pins 112 and 116 are the furthest away from each other for hinge 110. Support pins 114 and 118 are the closest to each other for hinge 110. Upper upright 22, 40 and lower upright 62, 80 reside at the largest arc A1. At this point, hinge 110 does not apply a force to the user's knee.

In FIG. 5B (middle flexion/extension), primary pins 112 and 116 have moved linearly towards each other to an approximate midpoint of travel for hinge 110. Support pins 114 and 118 have also moved to a midpoint of travel for hinge 110, but have moved away from each other and done so along curved paths. Upper upright 22, 40 and lower upright 62, 80 likewise reside at an approximate midpoint between the largest arc A1 and the smallest arc A2. At this point, hinge 110 is applying approximately half of its total potential compressive force capability to the user's knee.

In FIG. 5C (total extension), primary pins 112 and 116 have moved linearly towards each other as far as possible to an end-of-travel point for hinge 110. Support pins 114 and 118 have also moved to the travel endpoints for hinge 110 but have moved away from each other along the curved paths. Upper upright 22, 40 and lower upright 62, 80 reside now at the smallest arc A2. At this point, hinge 110 is applying all of its potential compressive force capability to the user's knee.

When the user's knee is subsequently bent from the extended position of FIG. 5C, hinge 110 moves from the position of FIG. 5C towards the position of FIG. 5A, reversing the pin and upright arc movement discussed above and relaxing the applied compressive force.

Referring now to FIGS. 6A to 6C, hinge 210 is shown alternatively expanding in an overall arc length struck as upper upright 22, 40 and lower upright 62, 80 are rotated from total flexion (FIG. 6A), to a midpoint of rotation (FIG. 6B), to total extension (FIG. 6C). The locations of pins 212, 214, 216 and 218 are also shown in each snapshot. The broken lines indicate the smallest arc A1 and the largest arc A2 struck by upper upright 22, 40 and lower upright 62, 80.

In FIG. 6A (total flexion), primary pins 212 and 216 are the closest to each other for hinge 210. Support pins 214 and 218 are the furthest apart from each other for hinge 210. Upper upright 22, 40 and lower upright 62, 80 reside at the smallest arc A1. At this point, hinge 210 does not apply a force to the user's knee.

In FIG. 6B (middle flexion/extension), primary pins 212 and 216 have moved linearly away from each other to an approximate midpoint of travel for hinge 210. Support pins 214 and 218 have also moved to a midpoint of travel for hinge 210, but have moved towards each other and have done so along curved paths. Upper upright 22, 40 and lower upright 62, 80 likewise reside at an approximate midpoint between the smallest arc A1 and the largest arc A2. At this point, hinge 210 is applying approximately half of its total potential tensile force capability to the user's knee.

In FIG. 6C (total extension), primary pins 212 and 216 have moved linearly away from each other as far as possible to an end-of-travel point for hinge 210. Support pins 214 and 218 have also moved to the travel endpoints for hinge 210, but have moved towards each other along the curved paths. Upper upright 22, 40 and lower upright 62, 80 reside now at the largest arc A2. At this point, hinge 210 is applying all of its potential compressive force capability to the user's knee.

When the user's knee is subsequently bent from the extended position of FIG. 6C, hinge 210 moves from the position of FIG. 6C towards the position of FIG. 6A, reversing the pin and upright arc movement just discussed and relaxing the applied tensile force.

Referring now to FIGS. 7A to 7C, brace 10 is shown being worn by the user who is at mid-stride, that is, extending his or her leg while walking or running. Consistent with FIG. 1, brace 10 is worn on the user's right leg, making FIG. 7A a lateral view, FIG. 7B a front view and FIG. 7B a medial view of the user's leg. Certain features of brace 10 have been removed from brace 10 of FIG. 1 merely for simplicity and ease of illustration. Features shown in FIGS. 7A to 7C have been numbered the same as above.

In the illustrated embodiment, extension (radially-increasing) hinge 210 is placed in the lateral position on brace 10, while contraction (radially-decreasing) hinge 110 is placed in the medial position on brace 10. As has been discussed herein, the position of hinges 110 and 210 on brace 10 can be reversed based on the user's condition. In mid-stride, the pins of hinges 110 and 210 are about halfway through their total travel. As shown above, this results in the corresponding uprights 22, 62, 40 and 80 being moved about half way through their total travel. The movement of the uprights in connection with the fixation of the uprights to the user's leg applies respective forces to the user's leg. With the brace fixed to the user's leg and the movement of the pins a mechanical certainty, the only structure remaining with room to give is the user's knee. It is intended that the resulting give in the knee be a corrective give. As discussed above, lateral upright 22 can be adjusted via sliding pieces 24 and 26 to heighten the corrective force or to relax the corrective force.

In the midpoint extension of FIGS. 7A to 7C, the resulting tensile force $F_T$ on the lateral side of the user's knee and compression force $F_C$ on the medial side of the user's knee are accordingly about half that of full extension of brace 10. It should be appreciated however that tensile force $F_T$ and compression force $F_C$ act together to create an overall force that, when viewed from the front view of FIG. 7B, will tend to open the knee joint on the lateral or left side of the user's knee and close the knee joint on the medial side of the user's knee during extension. Switching the location of hinges 110 and 210 will have the opposite overall effect, namely, tensile force $F_1$ and compression force $F_C$ will act together to create an overall force that, when viewed from the front view of FIG. 7B, will tend to want to open the knee joint on the medial or right side of the user's knee and close the knee joint on the lateral or left side of the user's knee. In either case, the adjustability of upright 22 (or other upright is desired) can heighten or lessen the torque-like overall force application.

FIGS. 8A to 8C show the user and brace 10 at full extension. The pins of hinges 110 and 210 are at the end of travel. Tensile force $F_T$ and compression force $F_C$ have now reached full potential to apply the maximum joint correction force when the joint is bearing the user's weight and correction is most needed. When the user is sitting with knees bent, the correction force is not needed and is advantageously relaxed.

Alternative Embodiments

In one alternative embodiment, the dynamic bracing feature is alternatively accomplished using a single extending or contracting hinge attached to upper and lower upright arms and two crisscrossing straps (one starting from each upright) that cross the knee opposite the side with the hinge and spiral in opposite directions, extending and attaching to the top or bottom of the opposing upright. One example of a suitable crisscrossing strap system is described in U.S. Pat. No. 7,198,610 ("the '610 Patent"), entitled, "Knee Brace And Method For Securing The Same", the entire contents of which are hereby incorporated by reference and relied upon. For example, prior art FIG. 1 of the '610 Patent shows a single hinge and upper and lower straps. Columns 1 and 2 of the '610 Patent discuss how forces are applied by the force straps, which forces are highlighted in prior art FIGS. 1 and 2 of the '610 Patent. The present disclosure contemplates exchanging the hinge of FIG. 1 of the '610 Patent with a dynamically contracting hinge, such as hinge 110, or dynamically extending hinge, such as hinge 210, discussed herein.

In another alternative embodiment, it may be found, e.g., for certain users, that the differential created between one of the dynamically changing hinges 110 and 210 in combination with a non-changing hinge provides a sufficient overall corrective force. It is accordingly expressly contemplated to replace either of the hinges in FIGS. 7A to 8C with a non-changing hinge, and wherein the remaining hinge is either one of contraction hinge 110 or extension hinge 210.

One suitable non-changing hinge is illustrated and described in the '610 Patent referenced above, which illustrates a polycentric hinge at FIGS. 61 and 62 and at columns 24 and 25 of the '610 Patent.

Figure 9:
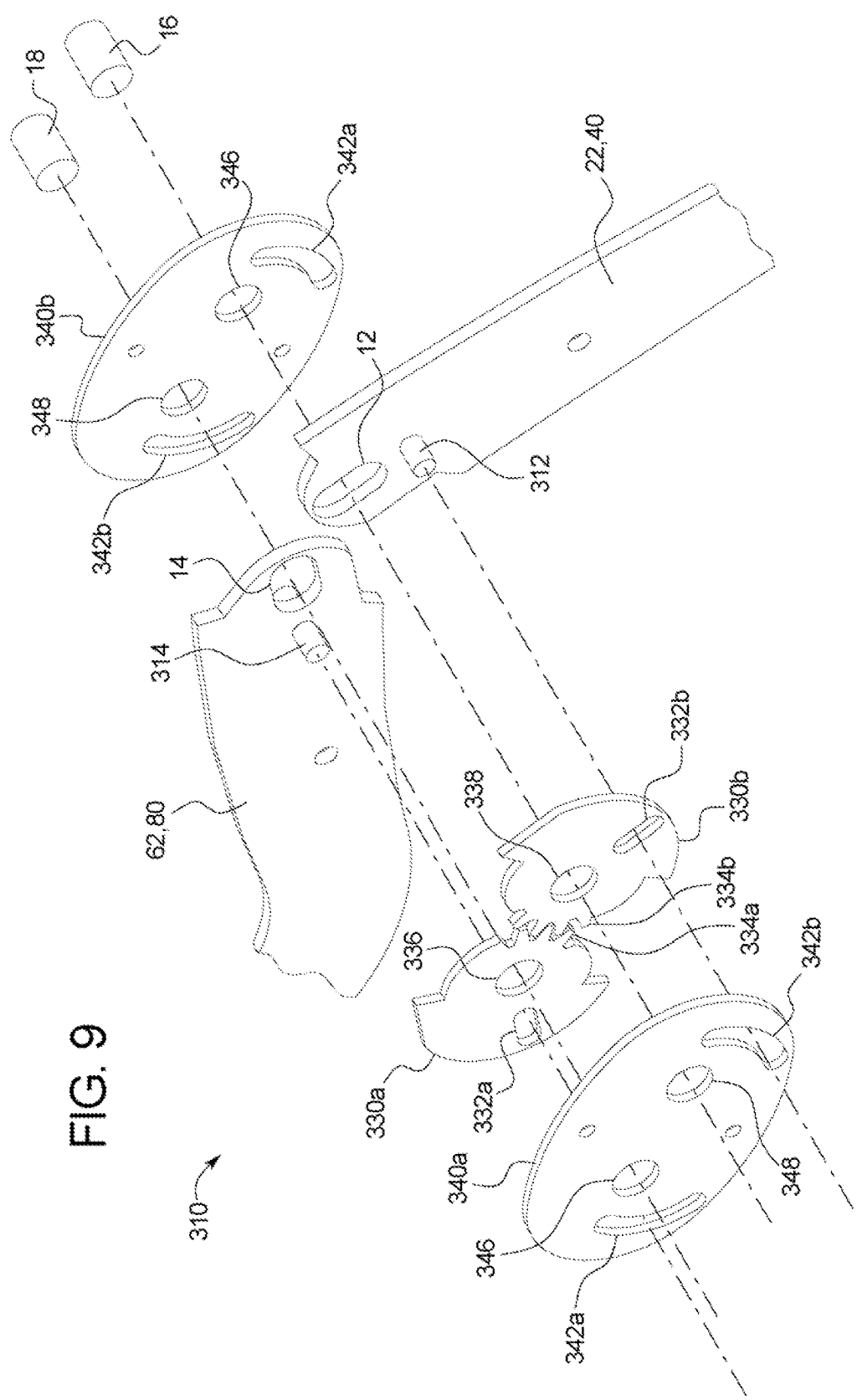
FIG. 9 is an exploded perspective view of another embodiment of a hinge that shortens or contracts in overall length as the brace moves from flexion to extension (bent position to extended position).
Figure 10:
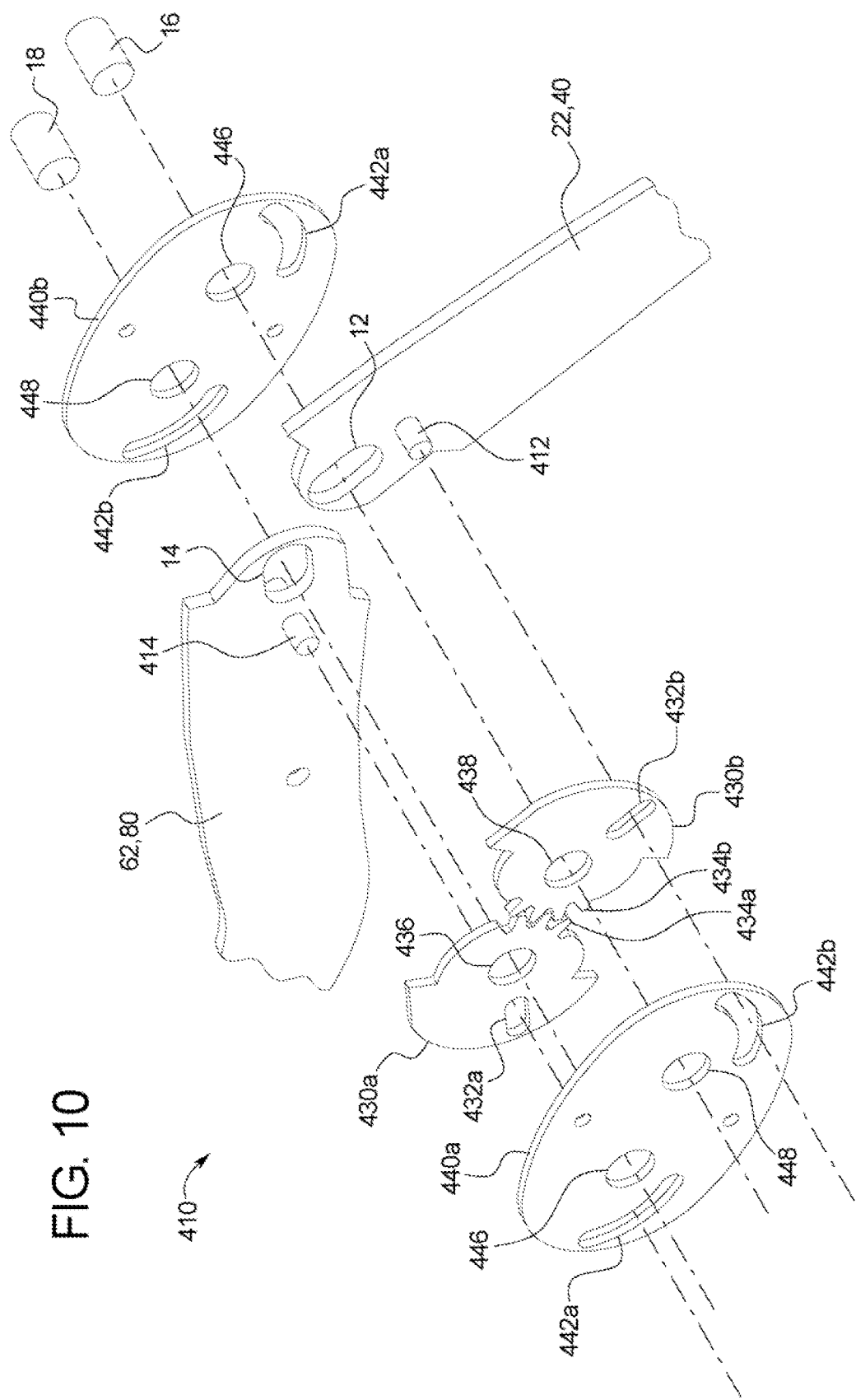
FIG. 10 is an exploded perspective view of another embodiment of a hinge that lengthens or expands in overall length as the brace moves from flexion to extension (bent position to extended position).

Referring now to FIGS. 9 and 10, in a further alternative embodiment, a dynamically changing polycentric mechanism is provided in place of the four-bar linkages of hinges 110 and 210. That is, one or both of hinges 110 and 210 can be replaced with either or both of the dynamic polycentric hinges (as long as the replacement results in one shortening and the other lengthening), where either or both of the medial and lateral hinges can be a dynamic polycentric hinge. A single dynamic polycentric hinge could alternatively be used for the medial or lateral hinge, while the other hinge is an above-described non-changing hinge.

In particular, FIG. 9 illustrates an embodiment of a contracting or shortening hinge 310, while FIG. 10 illustrates an embodiment of an expanding or lengthening hinge 410. Hinges 310 and 410 are each operable with lateral uprights 22, 62 or medial uprights 40, 80 as illustrated, which can be formed or constructed in any manner and of any material described herein. Upper upright 22, 40 is provided with a single pin 312 or 412, while lower uptight 62, 80 is provided with a single pin 314 or 414. The material, structure and placement of pins 312, 314, 412 and 414 can be in accordance with any of the alternatives described herein for pins 112, 114, 116, 118, 212, 214, 216 and 218. Wear plates, such as wear plates 120, 122, 124, 126, 222, 224, 226 and 228 are not shown in FIGS. 9 and 10 for ease of illustration but are indeed provided in any manner discussed herein in one embodiment. Upper upright 22, 40 and lower upright 62, 80 are formed with respective elongated slots 12 and 14. Slots 12 and 14 of the respective upper and lower uprights highlight one main difference between the polycentric hinges 310 and 410 and the four-bar hinges 110 and 210 discussed above. The uprights of the four-bar linkages each include two sets of pins. The uprights of the polycentric hinges 310 and 410 instead each include a single pin and a slot 12 or 14 that slides and rotates relative to a respective fastener 16 or 18 inserted through the hinges 310 and 410 to hold the hinges together.

As illustrated in FIG. 9, hinge 310 includes a first polycentric member 330a and a second polycentric member 330b. Members 330a and 330b can be made of any of the materials discussed above for four-bar linkage members 130a, 130b, 230a and 230b. Member 330a includes a straight slot 332a that slides and rotates relative to pin 314. Member 330a also defines a fastener receiving hole 336 for receiving fastener 18 (bolt, screw, rivet, barbed-connector, etc.) to hold the components of hinge 310 together. Member 330a further defines gear teeth 334a that mesh with gear teeth 334b of cooperating polycentric member 330b. Gear teeth 334a and 334b remain in geared contact throughout the rotation from flexion to extension (and vice versa) for hinge 310. Cooperating polycentric member 330b is the same as member 330a, defining a straight, pin 312 receiving slot 332b and a fastener receiving hole 338 for receiving fastener 16 (bolt, screw, rivet, barbed-connector, etc.), which also serves to hold the components of hinge 310 together.

Cover plates 340a and 340b are provided in one preferred embodiment to prevent contact with and to obscure the view of polycentric members 330a and 330b. Cover plates 340a and 340b can be made of any of the materials discussed above (plastic or metal) for any of the cover plates of hinge 110 and 210. Cover plates 340a and 340b each include or a define curved slot 342a and 342b, respectively, for directing the movement of one of pins 312 and 314 (and thus the movement of the uprights as illustrated in detail below in FIGS. 11A to 11C). Cover plates 340a and 340b also define fastener receiving holes 346 and 348 for receiving fasteners 16 or 18 to fasten hinge 310 together.

As illustrated in FIG. 10, hinge 410 likewise includes a first polycentric member 430a and a second polycentric member 430b. Members 430a and 430b can be made of any of the materials discussed above for four-bar linkage members 130a, 130b, 230a and 230b. Member 430a includes a straight slot 432a that slides and rotates relative to pin 414. Member 430a also defines a fastener receiving hole 436 for receiving fastener 18 (bolt, screw, rivet, barbed-connector, etc.) to hold the components of hinge 410 together. Member 430a further defines gear teeth 434a that mesh with gear teeth 434b of cooperating polycentric member 430b. Gear teeth 434a and 434b remain in geared contact throughout the rotation from flexion to extension (and vice versa) for hinge 410. Cooperating polycentric member 430b is the same as member 430a, defining a straight pin 412 receiving slot 432b and a fastener receiving hole 438 for receiving fastener 16 (bolt, screw, rivet, barbed-connector, etc.), which also helps to hold the components of hinge 410 together.

Cover plates 440a and 440b are provided in one preferred embodiment to prevent contact with and to obscure the view of polycentric members 430a and 430b. Cover plates 440a and 440b can be made of any of the materials discussed above (plastic or metal) for any of the cover plates of hinge 110 and 210. Cover plates 440a and 440b each include or define curved slots 442a and 442b for directing the movement of one of pins 412 and 414 (and thus the movement of the uprights as illustrated in detail below in FIGS. 12A to 12C). Cover plates 440a and 440b also define fastener receiving holes 446 and 448 for receiving fasteners 16 or 18 to fasten hinge 410 together. The primary difference between hinge 310 and hinge 410 is the shape and orientation of curved slots 342a and 342b versus curved slots 442a and 442b.

Referring now to FIGS. 11A to 11C, shortening polycentric hinge 310 is shown in total flexion striking arc A1 in FIG. 11A. Hinge 310 shortens to strike an arc between arcs A1 and A2 in FIG. 11B at approximately midway between total flexion and total extension. Hinge 310 further shortens to strike an arc at A2 in FIG. 11C at total extension. Unlike four-bar linkage hinges 110 and 210, polycentric hinges 310 and 410 use the fasteners 16 and 18 as stationary fulcrums. With hinge 310, gear teeth 334a and 334b rotate in geared contact respectively about the fulcrums of fasteners 16 and 18. Curved slots 342a and 342b of stationary hinge plates 340a and 340b are configured and arranged to guide the upright pins 312 and 314 inwardly as uprights 62, 80 and 22, 40 are unfolded from flexion to extension. Straight slots 12 and 14 of respective upper upright 22, 40 and lower upright 62, 80 allow the uprights to correspondingly move respectively inwardly towards each other relative to the spatially fixed relationship between fasteners 16 and 18, which extend through respective combined circular holes 348, 338, 346 (FIG. 9, looking front to back) and 346, 336, 348 (FIG. 9, looking front to back). Straight slots 332a and 332b of respective polycentric members 330a and 330b allow pin 314 of upright 62, 80 and pin 312 of upright 22, 40 to move respectively inwardly relative to the spatially fixed relationship between fasteners 16 and 18 during rotation from flexion to extension.

Referring now to FIGS. 12A to 12C, lengthening polycentric hinge 410 is shown in total flexion striking arc A1 in FIG. 12A. Hinge 410 lengthens to strike an arc between arcs A1 and A2 in FIG. 12B at approximately midway between total flexion and total extension. Hinge 410 further lengthens to strike an arc at A2 in FIG. 12C at total extension. Again, unlike four-bar linkage hinges 110 and 210, polycentric hinges 310 and 410 use the fasteners 16 and 18 as stationary fulcrums. As with hinge 310, gear teeth 434a and 434b of hinge 410 rotate in geared contact respectively about the fulcrums of fasteners 16 and 18. The different curved slots 442a and 442b of stationary hinge plates 440a and 440b are configured and arranged to guide the upright pins 412 and 414 outwardly as uprights 62, 80 and 22, 40 are unfolded from flexion to extension. Straight slots 12 and 14 of respective upper upright 22, 40 and lower upright 62, 80 allow the uprights to correspondingly move respectively outwardly away from each other relative to the spatially fixed relationship between fasteners 16 and 18, which extend through respective combined circular holes 448, 438, 446 (FIG. 10, looking front to back) and 446, 436, 448 (FIG. 10, looking front to back). Straight slots 432a and 432b of respective polycentric members 430a and 430b allow pin 414 of upright 62, 80 and pin 412 of upright 22, 40 to move respectively outwardly relative to the spatially fixed relationship between fasteners 16 and 18 during rotation from flexion to extension.

Additional Aspects of the Present Disclosure

Aspects of the subject matter described herein may be useful alone or in combination one or more other aspect described herein. Without limiting the foregoing description, in a first aspect of the present disclosure, an orthopedic knee brace includes an upper medial upright; a lower medial upright; an upper lateral upright; a lower lateral upright; a medial hinge connected rotatably to the upper and lower medial uprights; a lateral hinge connected rotatably to the upper and lower lateral, uprights; and wherein one of the medial and lateral hinges is configured such that its respective uprights rotate from a flexion to an extended relative positioning while striking a radially-decreasing arc, while the other of the medial and lateral hinges is configured such that its respective uprights rotate from a flexion to an extended relative positioning while striking a radially-increasing arc.

In a second aspect, which may be used with any other aspect herein, the radially-decreasing and radially-increasing arc hinges are each configured to be used as the medial hinge or the lateral hinge.

In a third aspect, which may be used with any other aspect herein, at least one of: (i) the upper medial and lateral uprights are in mechanical communication with each other; and (ii) the lower medial and lateral uprights are in mechanical communication with each other.

In a fourth aspect, which may be used with any other aspect herein, at least one of the uprights is adjustable in length.

In a fifth aspect, which may be used with any other aspect herein, the radially-decreasing arc hinge includes a first four-bar linkage and the radially-increasing hinge includes a second different four-bar linkage.

In a sixth aspect, which may be used with at least the fifth aspect, the first four-bar linkage is (i) connected to a first one of the uprights at a first primary pivot location and a first support pivot location, (ii) connected to a second one of the uprights at a second primary pivot location and a second support pivot location, and (iii) configured and arranged such that the first and second primary pivot locations move towards each other to form the radially-decreasing arc.

In a seventh aspect, which may be used with at least the sixth aspect, the first and second primary pivot locations are configured to move towards each other in a generally linear fashion.

In an eighth aspect, which may be used with at least the sixth aspect, the first four-bar linkage is configured and arranged such that the first and second support pivot locations move away from each other over the radially-decreasing arc.

In a ninth aspect, which may be used with at least the eighth aspect, the first and second support pivot locations are configured to move away from each other non-linearly.

In a tenth aspect, which may be used with at least the fifth aspect, the second four-bar linkage is (i) connected to a first one of the uprights at a first primary pivot location and a first support pivot location, (ii) connected to a second one of the uprights at a second primary pivot location and a second support pivot location, and (iii) configured and arranged such that the first and second primary pivot locations move away from each other to form the radially-increasing arc.

In an eleventh aspect, which may be used with at least the tenth aspect, the first and second primary pivot locations are configured to move away from each other in a generally linear fashion.

In an twelfth aspect, which may be used with at least the tenth aspect, the second four-bar linkage is configured and arranged such that the first and second support pivot locations move towards each other over the radially-increasing arc.

In a thirteenth aspect, which may be used with at least the twelfth aspect, the first and second support pivot locations are configured to move towards each other non-linearly.

In a fourteenth aspect, which may be used with at least the fifth aspect, the orthopedic knee brace includes a cover plate covering at least a portion of one of the first and second four-bar linkages, the cover plate including an area of decreased thickness arranged to accept movement of a member of one of the first and second four-bar linkages.

In a fifteenth aspect, which may be used with any other aspect herein, wherein the radially-decreasing arc hinge is a first polycentric hinge and the radially-increasing arc hinge is a second, different polycentric hinge.

In a sixteenth aspect, which may be used with any other aspect herein, an orthopedic knee brace includes an upper medial upright; a lower medial upright; an upper lateral upright; a lower lateral upright; a medial hinge connected rotatably to the upper and lower medial uprights: a lateral hinge connected rotatably to the upper and lower lateral uprights; and wherein a first one of the medial and lateral hinges is structured such that its respective uprights rotate from a flexion position to an extended position striking an arc that is increasingly different from an arc struck by the respective uprights of the second of the medial and lateral hinges rotating from the flexion position to the extended position.

In a seventeenth aspect, which may be used with at least the sixteenth aspect, the first one of the medial and lateral hinges strikes an increasingly changing arc, while the second one of the medial and lateral hinges strikes a static arc.

In an eighteenth aspect, which may be used with at least the sixteenth aspect, the first one of the medial and lateral hinges strikes an expanding arc, while the second one of the medial and lateral hinges strikes a contracting arc.

In a nineteenth aspect, which may be used with any other aspect herein, an orthopedic knee brace includes an upper medial upright; a lower medial upright; an upper lateral upright; a lower lateral upright; a medial hinge connected rotatably at a first pivot location to the upper medial upright and at a second pivot location to the lower medial upright; a lateral hinge connected rotatably at a first pivot location to the upper lateral upright and at a second pivot location to the lower lateral upright; and wherein a first one of the medial and lateral hinges is structured such that during movement from a flexion position to extended position, its respective first and second pivot locations move relative to each other differently than the respective first and second pivot locations of the other of the medial and lateral hinges during movement from the flexion position to the extended position.

In a twentieth aspect, which may be used with at least the nineteenth aspect, the first and second pivot locations of the first one of the medial and lateral hinges move towards or away from each other, while the first and second pivot locations of the other of the medial and lateral hinges are generally static with respect to each other.

In a twenty-first aspect, which may be used with at least the nineteenth aspect, the first and second pivot locations for the first one of the medial and lateral hinges move towards each other, while the first and second pivot locations for the other of the medial and lateral hinges move away from each other.

In a twenty-second aspect, which may be used with any other aspect herein, either one of the medial and lateral hinges and its respective upright can be replaced with a strapping arrangement.

In a twenty-third aspect, any of the structure and functionality illustrated and described in connection with FIG. 1 may be used with any other aspect herein.

In a twenty-fourth aspect, any of the structure and functionality illustrated and described in connection with FIG. 2 may be used with any other aspect herein.

In a twenty-fifth aspect, any of the structure and functionality illustrated and described in connection with FIG. 3 may be used with any other aspect herein.

In a twenty-sixth aspect, any of the structure and functionality illustrated and described in connection with FIG. 4 may be used with any other aspect herein.

In a twenty-seventh aspect, any of the structure and functionality illustrated and described in connection with FIGS. 5A to 5C may be used with any other aspect herein.

In a twenty-eighth aspect, any of the structure and functionality illustrated and described in connection with FIGS. 6A to 6C may be used with any other aspect herein.

In a twenty-ninth aspect, any of the structure and functionality illustrated and described in connection with FIGS. 7A to 7C may be used with any other aspect herein.

In a thirtieth aspect, any of the structure and functionality illustrated and described in connection with FIGS. 8A to 8C may be used with any other aspect herein.

In a thirty-first aspect, any of the structure and functionality illustrated and described in connection with FIG. 9 may be used with any other aspect herein.

In a thirty-second aspect, any of the structure and functionality illustrated and described in connection with FIG. 10 may be used with any other aspect herein.

In a thirty-third aspect, any of the structure and functionality illustrated and described in connection with FIGS. 11A to 11C may be used with any other aspect herein.

In a thirty-fourth aspect, any of the structure and functionality illustrated and described in connection with FIGS. 12A to 12C may be used with any other aspect herein.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An orthopedic knee brace comprising:
an upper medial upright;
a lower medial upright;
an upper lateral upright;
a lower lateral upright;
a medial hinge connected rotatably to the upper and lower medial uprights;
a lateral hinge connected rotatably to the upper and lower lateral uprights; and
wherein one of the medial and lateral hinges is configured to pull each of its respective uprights inwardly as its uprights rotate from a flexion to an extended relative positioning while striking a radially-decreasing arc radius, while the other of the medial and lateral hinges is configured to push each of its respective uprights outwardly as its uprights rotate from a flexion to an extended relative positioning while striking a radially-increasing arc radius.

2. The orthopedic knee brace of claim 1, wherein the medial hinge or the lateral hinge includes a first four-bar linkage and the other of the medial hinge or the lateral hinge includes a second different four-bar linkage.

3. The orthopedic knee brace of claim 2, wherein the second four-bar linkage is (i) connected to a first one of the upper medial upright, the upper lateral upright, the lower medial upright or the lower lateral upright at a first primary pivot location and a first support pivot location, (ii) connected to a remaining one of the upper medial upright, the upper lateral upright, the lower medial upright or the lower lateral upright at a second primary pivot location and a second support pivot location, and (iii) configured and arranged such that the first and second primary pivot locations move away from each other to push the uprights outwardly and form the radially-increasing arc radius.

4. The orthopedic knee brace of claim 3, wherein the second four-bar linkage is configured and arranged such that the first and second support pivot locations move towards each other over the radially-increasing arc radius.

5. The orthopedic knee brace of claim 4, wherein the first and second support pivot locations are configured to move towards each other non-linearly.

6. The orthopedic knee brace of claim 3, wherein the first and second primary pivot locations are configured to move away from each other in a generally linear fashion.

7. The orthopedic knee brace of claim 2, wherein the first four-bar linkage is (i) connected to a first one of the upper medial upright, the upper lateral upright, the lower medial upright or the lower lateral upright at a first primary pivot location and a first support pivot location, (ii) connected to a remaining one of the upper medial upright, the upper lateral upright, the lower medial upright or the lower lateral upright at a second primary pivot location and a second support pivot location, and (iii) configured and arranged such that the first and second primary pivot locations move towards each other to pull the uprights inwardly and form the radially-decreasing arc radius.

8. The orthopedic knee brace of claim 7, wherein the first four-bar linkage is configured and arranged such that the first and second support pivot locations move away from each other over the radially-decreasing arc radius.

9. The orthopedic knee brace of claim 8, wherein the first and second support pivot locations are configured to move away from each other non-linearly.

10. The orthopedic knee brace of claim 7, wherein the first and second primary pivot locations are configured to move towards each other in a generally linear fashion.

11. The orthopedic knee brace of claim 1, wherein the medial hinge or the lateral hinge includes a first four-bar linkage and the other of the medial hinge or the lateral hinge includes a second, different four-bar linkage, the first four-bar linkage including a first inner cover plate and a first outer cover plate, the first inner cover plate and the first outer cover plate encapsulating the first four-bar linkage, and the second, different four-bar linkage including a second inner cover plate and a second outer cover plate, the second inner cover plate and the second outer cover plate encapsulating the second, different four-bar linkage.

12. The orthopedic knee brace of claim 1, wherein at least one of: (i) the upper medial upright and the upper lateral upright are in mechanical communication with each other; and (ii) the lower medial upright and the lower lateral upright are in mechanical communication with each other.

13. The orthopedic knee brace of claim 1, wherein at least one of the upper medial upright, the lower medial upright, the upper lateral upright, or the lower lateral upright is adjustable in length.

14. The orthopedic knee brace of claim 2, which includes a cover plate covering at least a portion of one of the first and second four-bar linkages, the cover plate including an area of decreased thickness arranged to accept movement of a member of one of the first and second four-bar linkages.

15. The orthopedic knee brace of claim 1, wherein one of the medial hinge or the lateral hinge is a first polycentric hinge and the other of the medial hinge or the lateral hinge is a second, different polycentric hinge.

* * * * *